(12) United States Patent
Itagaki et al.

(10) Patent No.: US 9,063,207 B2
(45) Date of Patent: Jun. 23, 2015

(54) MAGNETIC RESONANCE IMAGING APPARATUS AND BLOOD VESSEL IMAGE CAPTURING METHOD

(75) Inventors: Hiroyuki Itagaki, Tokyo (JP); Nobuyuki Yoshizawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 164 days.

(21) Appl. No.: 13/641,161

(22) PCT Filed: Apr. 14, 2011

(86) PCT No.: PCT/JP2011/059230
§ 371 (c)(1),
(2), (4) Date: Oct. 15, 2012

(87) PCT Pub. No.: WO2011/132593
PCT Pub. Date: Oct. 27, 2011

(65) Prior Publication Data
US 2013/0034287 A1     Feb. 7, 2013

(30) Foreign Application Priority Data

Apr. 20, 2010  (JP) ................................ 2010-096688
Mar. 22, 2011  (JP) ................................ 2011-062752

(51) Int. Cl.
| G06K 9/00 | (2006.01) |
| G01R 33/563 | (2006.01) |
| A61B 5/02 | (2006.01) |
| A61B 5/026 | (2006.01) |

(Continued)

(52) U.S. Cl.
CPC ...... *G01R 33/56316* (2013.01); *A61B 5/02007* (2013.01); *G01R 33/4838* (2013.01); *G01R 33/5617* (2013.01); *G01R 33/5635* (2013.01);
*A61B 5/7285* (2013.01); *A61B 5/0263* (2013.01); *A61B 5/0456* (2013.01)

(58) Field of Classification Search
None
See application file for complete search history.

(56) References Cited

U.S. PATENT DOCUMENTS

| 2003/0166999 A1 | 9/2003 | Liu et al. |
| 2009/0069668 A1* | 3/2009 | Stemmer ....................... 600/413 |
| 2009/0143666 A1* | 6/2009 | Edelman et al. .............. 600/410 |

FOREIGN PATENT DOCUMENTS

| JP | 2003-135430 | 5/2003 |
| JP | 2004-535869 | 12/2004 |

(Continued)

OTHER PUBLICATIONS

Boettger et al ("Radiation therapy planning and simulation with magnetic resonance images", Medical Imaging 2008).*

(Continued)

*Primary Examiner* — Avinash J Yentrapati
(74) *Attorney, Agent, or Firm* — Cooper & Dunham LLP

(57) ABSTRACT

There is provided an MRI apparatus and a blood vessel image capturing method capable of improving the separability of an artery and a vein. In order to do so, using an imaging sequence obtained by combining a first sequence portion for measuring a first echo signal used for acquisition of a blood vessel image of a desired region of an object with a second sequence portion for measuring a second echo signal used for acquisition of blood flow information of the object, the object is imaged by one examination scan. In addition, blood flow information is acquired using the second echo signal, and at least one of an artery and a vein is extracted in an image, which is reconstructed using the first echo signal, using the acquired blood flow information.

8 Claims, 18 Drawing Sheets

(51) Int. Cl.
*G01R 33/483* (2006.01)
*G01R 33/561* (2006.01)
*A61B 5/00* (2006.01)
*A61B 5/0456* (2006.01)

(56) References Cited

FOREIGN PATENT DOCUMENTS

| JP | 2009-160052 | 7/2009 |
| JP | 2010-63871 | 3/2010 |

OTHER PUBLICATIONS

International search report dated Jul. 5, 2011 in corresponding PCT Application No. PCT/JP 2011/059230.

Feb. 17, 2015 Japanese official action in corresponding Japanese Patent Application No. 2012-511628.

\* cited by examiner

FIG. 2
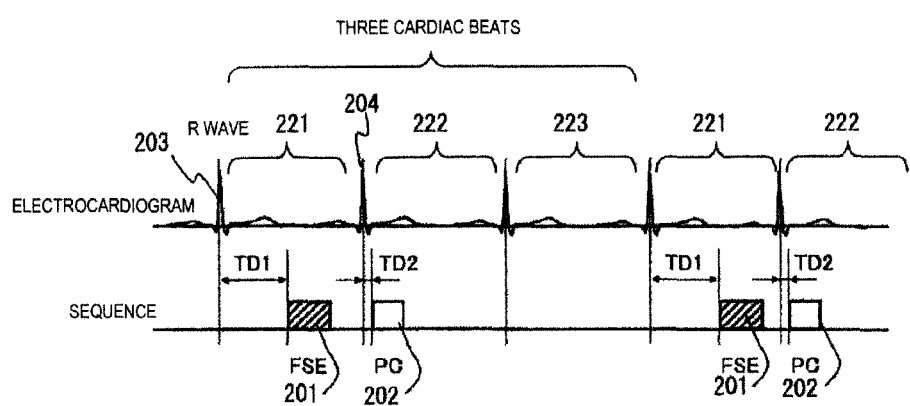
(a)
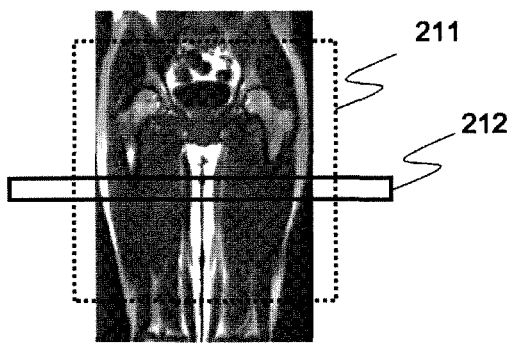
(b)

FIG. 13
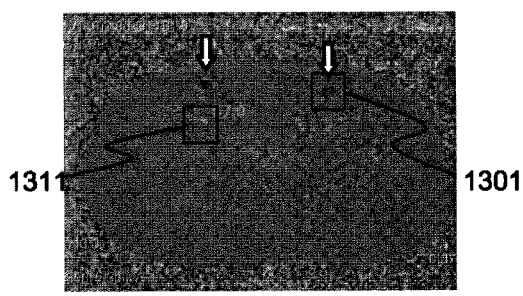
(a)
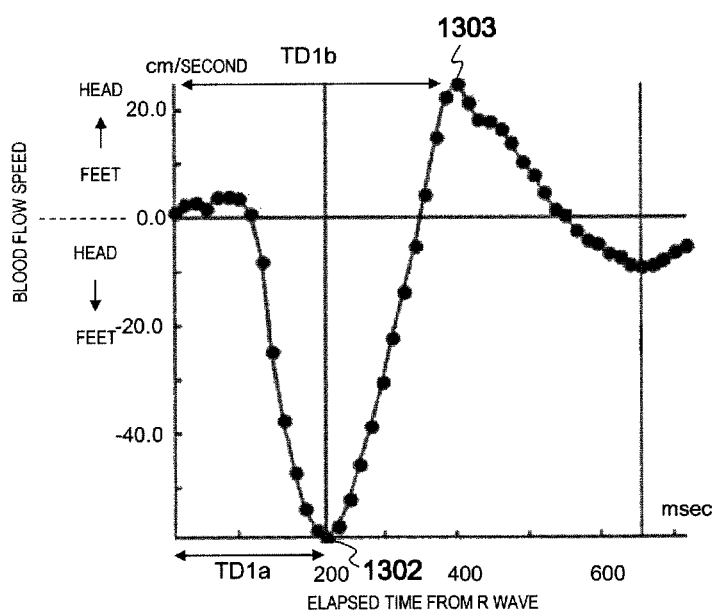
(b)

FIG. 16
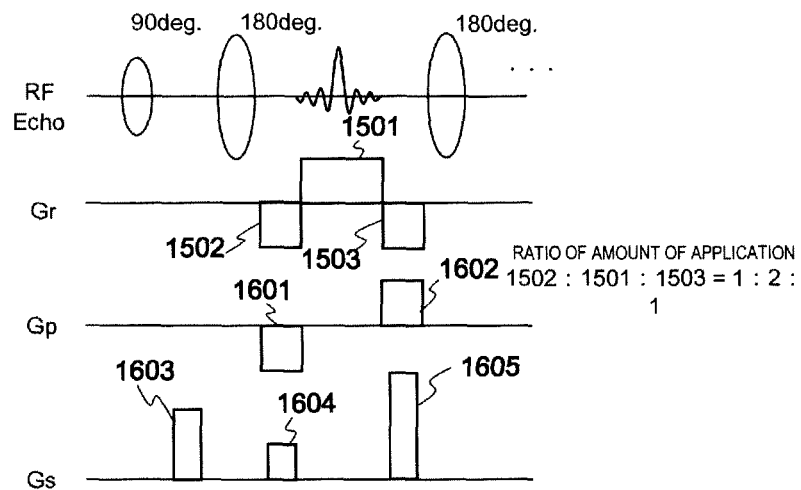
(a)
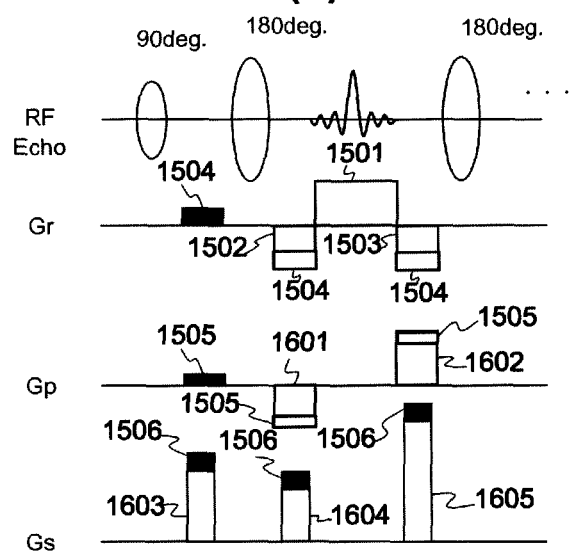
(b)

MAGNETIC RESONANCE IMAGING APPARATUS AND BLOOD VESSEL IMAGE CAPTURING METHOD

TECHNICAL FIELD

The present invention relates to a magnetic resonance imaging (hereinafter, referred to as an "MRI") apparatus and in particular, to a technique for imaging a blood vessel image of the object and extracting an artery and a vein in the blood vessel image.

BACKGROUND ART

The MRI apparatus is an apparatus which measures a nuclear magnetic resonance (NMR) signal generated by the object, especially, the spin of nuclei which form human tissue, and images the shapes or functions of the head, abdomen, limbs, and the like in a two-dimensional manner or in a three-dimensional manner. In the imaging, different phase encoding is given to NMR signals by the gradient magnetic field and frequency encoding is also given to the NMR signals, and the NMR signals are measured as time-series data. The measured NMR signals are reconstructed as an image by a two-dimensional or three-dimensional Fourier transform.

Techniques for capturing a blood vessel image of an object without using a contrast medium (hereinafter, referred to as non-contrast MRA techniques) have been put to practical use in the MRI apparatus. For example, there are techniques disclosed in PTL 1 to PTL 4. In the imaging techniques in PTL 1 to PTL 4, the following steps (a) and (b) are executed in an examination scan.

(a) Under electrocardiographic synchronization, echo signals equivalent to the predetermined amount of slice encoding are collected using a high-speed spin echo (hereinafter, referred to as FSE) sequence. The FSE sequence is repeated every plural cardiac beats in a predetermined signal acquisition time (Acquisition Time, AT) after predetermined delay time (Delay Time, DT) from the electrocardiographic synchronization signal.

(a-1) DT and AT are adjusted, and the signal acquisition time of the FSE sequence is set in systole. In addition, a gradient magnetic field pulse (dephase pulse) which causes large phase dispersion in the spin of an artery with high blood flow speed and does not cause large phase dispersion in the spin of a vein with low blood flow speed is applied in a predetermined gradient magnetic field direction. By the application of this dephase pulse, echo signals from the artery with high blood flow speed are suppressed, thereby acquiring a vein image.

(a-2) DT and AT are adjusted, and the signal acquisition time of the FSE sequence is set in diastole. In addition, a gradient magnetic field pulse (rephase pulse) to compensate for the phase dispersion due to the blood flow speed is applied in a predetermined gradient magnetic field direction. As a result, an arteriovenous image in which an artery image and a vein image are included is acquired.

(b) A difference image is created using the data of the vein image acquired in (a-1) and the arteriovenous image acquired in (a-2). When creating the difference image, weighted differential processing is performed as necessary. For example, the signal strength of a diastolic image is multiplied by a predetermined weighting coefficient, for example, 0.8, and then a difference between the resultant image and the systolic image is calculated. As a result, the vein image is removed from the arteriovenous image, and the artery image can be acquired. A constant set in advance on the basis of experience or the like or the value input by the user is used as a weighting coefficient used for weighting.

Before the above step (a), it is necessary to perform a preparatory scan of the following (c). (c) A preparatory scan is performed before the FSE sequence of (a) using the imaging conditions of lower spatial resolution than the FSE sequence of this measurement of (a), thereby acquiring an image for each cardiac time phase. The user observes an image for each cardiac time phase of the preparatory scan, and selects as a systolic image an image in which only the vein image appears on the highest signal and selects as a diastolic image an image in which both the vein image and the artery image appear on the highest signal. DT and AT are determined such that the above FSE sequence of (a-1) is performed in the cardiac time phase of the selected systolic image. Similarly, DT and AT are determined such that the above FSE sequence of (a-2) is performed in the cardiac time phase of the selected diastolic image.

In addition, the FSE sequence by which a high-quality image is acquired is disclosed in PTL 5, for example.

On the other hand, as a non-contrast MRA technique, a PC (Phase Contrast) method is widely known by PTL 6 to PTL 8 and the like. The PC method is an imaging method of using the phenomenon in which when a bipolar gradient magnetic field that is a pair of gradient magnetic field pulses with the opposite polarities and the same magnitude is applied, a phase change according to the blood flow speed occurs in the spin in tissue with flow speed, such as a blood flow, while no phase change occurs in stationary tissue. By performing imaging while applying a bipolar gradient magnetic field in a predetermined direction, a change in the phase of a blood flow portion is obtained as an image. By inverting the polarity of the bipolar gradient magnetic field pulse, two images are obtained eventually. By calculating the difference to remove a signal of the stationary portion, an image of only the blood flow portion can be acquired. The pixel value of the image corresponds to the flow speed of the blood flow.

CITATION LIST

Patent Literature

[PTL 1] Japanese Patent No. 4090619
[PTL 2] Japanese Patent No. 4253411
[PTL 3] Japanese Patent No. 3434816
[PTL 4] Japanese Patent No. 4309632
[PTL 5] JP-A-5-168607
[PTL 6] JP-A-6-296600
[PTL 7] JP-A-7-59747
[PTL 8] JP-A-8-38444

SUMMARY OF INVENTION

Technical Problem

As described above, in the imaging techniques disclosed in the techniques of PTL 1 to PTL 4, a user selects systole and diastole while observing the image obtained by performing a preparatory scan as in the above-described step (c), and DT or AT of the FSE sequence is determined on the basis of this. These greatly depend on the user's determination. For this reason, there are problems in that the load on the user is large and the image state of a blood vessel image obtained by the user varies. In addition, if DT or AT is a constant set in advance, neither DT nor AT can be determined according to the state of the object.

In addition, a constant set in advance or the value input by the user is used as the weighting coefficient when calculating a difference image between an arteriovenous image and a vein image in the above-described step (b). Accordingly, in order to acquire an optimal difference image (artery image) according to the state of the object, the user needs to set the weighting coefficient by trial and error while observing the image state so that the vein image is removed.

In addition, in step (a-1), a dephase pulse is applied in order to disperse the phase of arterial blood flow with high flow speed. In the case of a peripheral part, however, not only the phase of a signal in the artery but also the phase of a signal in the vein is dispersed since a difference between the blood flow speed of the artery and the blood flow speed of the vein is small. As a result, since an image of a vein cannot be acquired, an image in which an artery image and a vein image are mixed is obtained even if the difference image is calculated in step (b). For this reason, it is difficult to acquire an artery image of the peripheral part of the object.

Therefore, it is an object of the present invention to provide an MRI apparatus and a blood vessel image capturing method capable of improving the separability of an artery and a vein according to the state of the object.

Solution to Problem

In order to achieve the above-described object, the present invention is characterized in that a plurality of images with different characteristics are captured using different imaging methods and a blood vessel image in which an artery and a vein are separated on one image is acquired by post-processing using the plurality of images with different characteristics. Specifically, an object is imaged by one examination scan using an imaging sequence obtained by combining a first sequence portion for measuring a first echo signal, which is used for acquisition of a blood vessel image of a desired region of the object, with a second sequence portion for measuring a second echo signal, which is used for acquisition of the blood flow information of the object. Then, the blood flow information is acquired using the second echo signal, and at least one of an artery and a vein is extracted on an image, which is reconstructed using the first echo signal, using the acquired blood flow information.

Therefore, an MRI apparatus of the present invention includes: a measurement control section which controls measurement of an echo signal from a desired region of an object using a predetermined imaging sequence; and an image reconstruction section which reconstructs an image using the echo signal. The imaging sequence is obtained by combining a first sequence portion for measuring a first echo signal used for acquisition of an image with a second sequence portion for measuring a second echo signal used for acquisition of blood flow information of the object. In addition, the MRI apparatus of the present invention further includes: a blood flow information acquisition section which acquires the blood flow information using the second echo signal; and an artery and vein separation section which extracts at least one of an artery and a vein in the image, which is reconstructed using the first echo signal, using the blood flow information.

In addition, a blood vessel image capturing method of the present invention includes: a measurement step of measuring first and second echo signals by repeating an imaging sequence in synchronization with periodic body motion of an object; a blood flow information acquisition step of acquiring blood flow information using the second echo signal; and a blood vessel image acquisition step of extracting at least one of an artery and a vein in an image, which is reconstructed using the first echo signal, using the blood flow information.

In addition, an MRI apparatus according to another aspect of the present invention includes: a measurement control section which controls measurement of an echo signal from a desired region of an object using a predetermined imaging sequence; an image reconstruction section which reconstructs an image using the echo signal; and an artery-and-vein-separated image creation section which creates an image in which at least one of an artery and a vein is extracted. The imaging sequence includes a first sequence portion for measuring an echo signal used for acquisition of an image and a second sequence portion for measuring an echo signal used for acquisition of blood flow information of the object. The artery-and-vein-separated image creation section executes the second sequence portion earlier than the first sequence portion, sets an imaging parameter of the first sequence portion using the acquired blood flow information of the object, and creates an image, in which at least one of an artery and a vein is extracted, from an echo signal obtained by executing the first sequence portion.

In addition, in a blood vessel image capturing method according to still another aspect of the present invention, a second sequence for measuring an echo signal used for acquisition of blood flow information of an object is performed, systole and diastole of a cardiac cycle are set using the acquired blood flow information, and a first sequence is performed in each of the systole and the diastole. A systolic image and a diastolic image are created from the acquired echo signals, and an image in which at least one of an artery and a vein is extracted is created by taking a difference between both the images.

Advantageous Effects of Invention

According to the MRI apparatus and the blood vessel image capturing method of the present invention, it is possible to improve the separability of an artery and a vein according to the state of the object.

BRIEF DESCRIPTION OF DRAWINGS

FIG. 2(a) is a view showing a timing chart of an imaging sequence related to a first embodiment, and FIG. 2(b) is a view showing an imaging region when imaging a leg region by the sequence in FIG. 2(a).

FIG. 6(a) is a flow chart showing the artery extraction process flow and FIG. 6(b) is a flow chart showing the vein extraction process flow.

FIG. 9(a) shows an example of region setting when detecting an artery selectively and FIG. 9(b) shows an example of region setting when detecting a vein selectively.

FIG. 13(a) is a view showing an image example of a pelvic region obtained by the PC method sequence in the fourth embodiment, and FIG. 13(b) is a graph drawn from an image obtained by the PC method sequence in the fourth embodiment.

FIG. 16(a) is a sequence chart showing a sequence for diastole obtained by adding Flow-comp pulses 1502 and 1503 to the FSE method sequence in FIG. 15, and FIG. 16(b) is a sequence chart showing a sequence for systole obtained by adding the Flow-comp pulses 1502 and 1503, a Flow-void pulse 1504, and the like to the FSE method sequence in FIG. 15.

DESCRIPTION OF EMBODIMENTS

Figure 1:
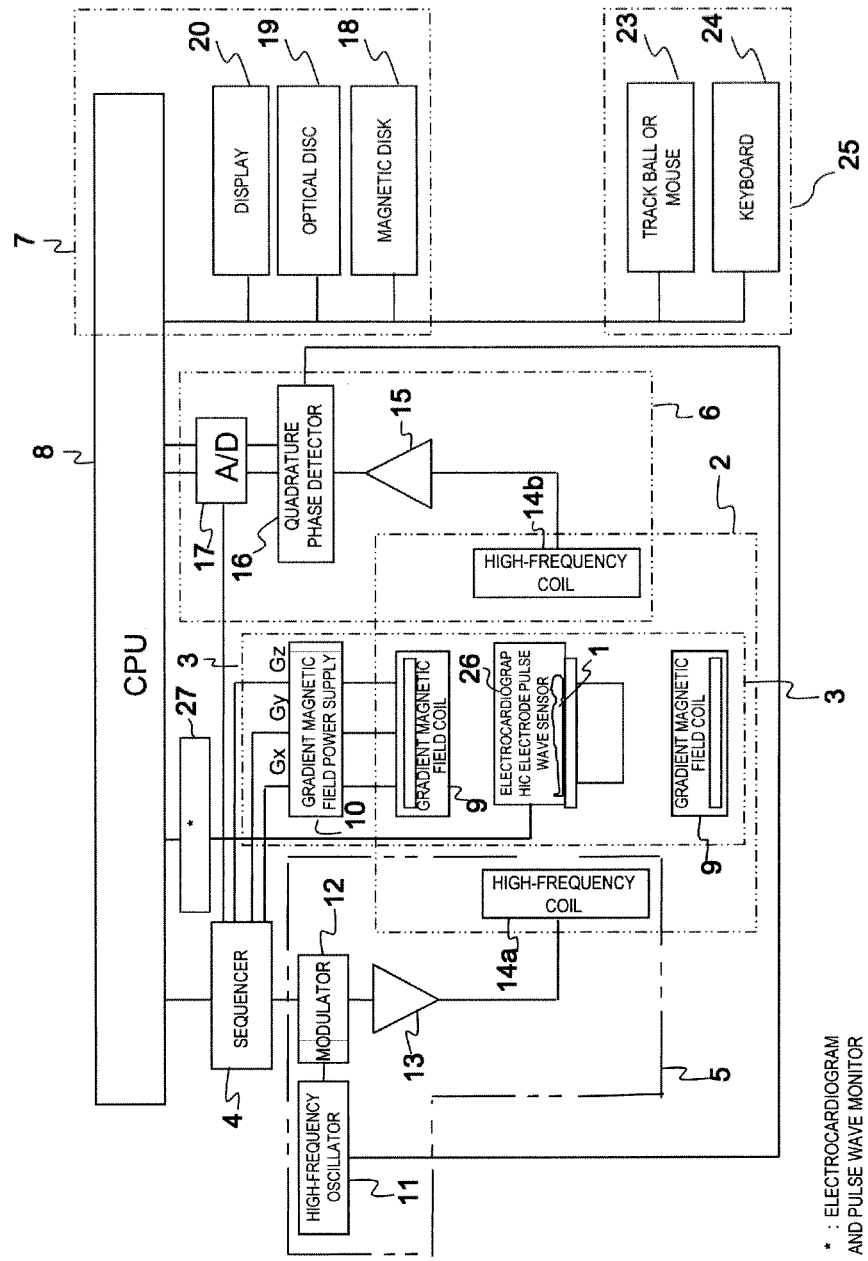
FIG. 1 is a block diagram showing the overall configuration of an example of an MRI apparatus related to the present invention.

Hereinafter, preferred embodiments of an MRI apparatus of the present invention will be described in detail according to the accompanying drawings. In addition, in all drawings for explaining the embodiments of the invention, the same reference numerals are given to those with the same functions and repeated explanation thereof will be omitted.

First, the outline of an example of an MRI apparatus related to the present invention will be described on the basis of FIG. 1. FIG. 1 is a block diagram showing the overall configuration of an embodiment of the MRI apparatus related to the present invention. This MRI apparatus acquires a tomographic image of an object using an NMR phenomenon. As shown in FIG. 1, the MRI apparatus is configured to include a static magnetic field generation system 2, a gradient magnetic field generation system 3, a signal transmission system 5, a signal receiving system 6, a signal processing system 7, a sequencer 4, and a central processing unit (CPU) 8.

The static magnetic field generation system 2 may be of a vertical magnetic field type or may be a horizontal magnetic field type. In any case, the static magnetic field generation system 2 is configured to include a permanent magnet type, normal conduct on type, or superconducting type magnetic field generation source disposed around an object 1. In the case of the vertical magnetic field type, the static magnetic field generation system 2 generates a uniform static magnetic field in the space around the object 1 in a direction perpendicular to the body axis. In the case of the horizontal magnetic field type, the static magnetic field generation system 2 generates a uniform static magnetic field in the body axis direction.

The gradient magnetic field generation system 3 includes a gradient magnetic field coil 9 which applies a gradient magnetic field in three axial directions of X, Y, and Z, which are a coordinate system (stationary coordinate system) of the MRI apparatus, and a gradient magnetic field power supply 10 which drives each gradient magnetic field coil. The gradient magnetic field power supply 10 of each coil is driven according to a command from a sequencer 4, which will be described later, so that the gradient magnetic fields Gx, Gy, and Gz in three axial directions of X, Y, and Z are applied. At the time of photographing, a slice-direction gradient magnetic field pulse (Gs) is applied in a direction perpendicular to the slice surface (cross section of photographing) so that a slice surface of the object 1 is set, and a phase-encoding-direction gradient magnetic field pulse (Gp) and a frequency-encoding-direction gradient magnetic field pulse (Gf) are applied in the two remaining directions, which are perpendicular to the slice surface and are also perpendicular to each other, so that the positional information in each direction is encoded in an echo signal.

The sequencer 4 is a measurement control unit that repeatedly controls the application of a high-frequency magnetic field pulse (hereinafter, referred to as an "RF pulse") and a gradient magnetic field pulse and measurement of an echo signal, which is generated by the object, on the basis of a predetermined pulse sequence. The sequencer 4 operates by control of the CPU 8, and transmits various commands, which are required for data collection of a tomographic image of the object 1, to the signal transmission system 5, the gradient magnetic field generation system 3, and the signal receiving system 6 in order to control them. Type and parameters of a pulse sequence are transmitted from the CPU 8 to the sequencer 4.

The signal transmission system 5 emits an RF pulse to the object 1 in order to cause an NMR phenomenon in the nuclear spins of atoms which form the body tissue of the object 1, and includes a high-frequency oscillator 11, a modulator 12, a high-frequency amplifier 13, and a transmission-side high-frequency coil (transmission coil) 14a. An RF pulse output from the high-frequency oscillator 11 is amplitude-modulated by the modulator 12 at the timing based on the command from the sequencer 4, and the amplitude-modulated high-frequency pulse is amplified by the high-frequency amplifier 13 and is then supplied to the high-frequency coil 14a disposed adjacent to the object 1. As a result, an RF pulse is emitted from the high-frequency coil 14a to the object 1.

The signal receiving system 6 detects an echo signal (NMR signal) emitted by nuclear magnetic resonance of the nuclear spins, which form the body tissue of the object 1, and includes a receiving-side high-frequency coil (receiving coil) 14b, a signal amplifier 15, a quadrature phase detector 16, and an A/D converter 17. The NMR signal of the response of the object 1 induced by electromagnetic waves emitted from the transmission-side high-frequency coil 14a is detected by the high-frequency coil 14b disposed adjacent to the object 1 and amplified by the signal amplifier 15. Then, at the timing based on the command from the sequencer 4, the signal is divided into two signals perpendicular to each other by the quadrature phase detector 16, and each of the signals is converted into a digital amount by the A/D converter 17 and transmitted to the signal processing system 7.

The signal processing system 7 performs display, saving, and the like of various kinds of data processing and processing results, and includes an external storage device, such as an optical disc 19 or a magnetic disk 18, and a display 20, such as a CRT. When the data from the signal receiving system 6 is input to the CPU (arithmetic processing unit) 8, the CPU 8 executes processing, such as signal processing and image reconstruction, and displays a tomographic image of the object 1, which is the result, on the display device 20 and also records the tomographic image on the magnetic disk 18 or the like of the external storage device.

An operating unit 25 is used when a user inputs various kinds of control information of the MRI apparatus or control information of processing performed by the signal processing system 7, and includes a trackball or mouse 23 and a keyboard 24. This operating unit 25 is disposed adjacent to the display 20, so that the operator controls various kinds of processing of the MRI apparatus interactively through the operating unit 25 while observing the display 20.

Moreover, in FIG. 1, the transmission-side high-frequency coil 14a and the gradient magnetic field coil 9 are disposed in the static magnetic field space of the static magnetic field generation system 2, in which the object 1 is inserted, such that they face the object 1 in the case of a vertical magnetic field method and they surround the object 1 in the case of a horizontal magnetic field method. In addition, the receiving-side high-frequency coil 14b is provided so as to face or surround the object 1.

An electrocardiogram and pulse wave monitor 27 receives a signal from a sensor unit attached to the object and processes the signal (for example, filtering and A/D conversion), and notifies the CPU 8 of the processing result. For example, when detecting an electrocardiogram of the object, an electrode which is a sensor unit is attached to the chest, limbs, or the like of the object, and the electrocardiogram and pulse wave monitor 27 processes a signal from each electrode and mainly detects an R wave of an electrocardiogram. When detecting a pulse wave, an infrared sensor is attached to the fingertip of the object, and electrocardiogram and pulse wave monitor 27 processes a signal from the infrared sensor and mainly detects a pulsation of a blood flow.

Nuclides imaged by current MRI apparatuses, which are widely used clinically, have a hydrogen nucleus (proton) which is a main constituent material of the object. The shapes or functions of the head, abdomen, limbs, and the like of the human body are imaged in a two-dimensional or three-dimensional manner by performing imaging of the spatial distribution of the proton density or the information regarding the spatial distribution of the relaxation time of the excited state.

(Outline of the Present Invention)

The present invention acquires images with different characteristics using two imaging methods. In this case, an artery and a vein are separated from each other on the other image by processing an image obtained by the other imaging method using the information of an imaging part of an object obtained by processing an image based on one imaging method. In this manner, an artery and a vein can be separated from each other depending on the state of an imaging part of an object. As a result, it is possible to acquire an image by separating an artery from a vein with high accuracy.

First Embodiment

Outline of an Invention of a First Embodiment

In the invention of the first embodiment, a plurality of images with different characteristics are captured using different imaging methods, and a blood vessel image in which an artery and a vein are separated from each other on one image is obtained by post-processing using the plurality of images different characteristics.

Specifically, an object imaged by one examination scan using an imaging sequence obtained by combining a first sequence portion for measuring a first echo signal, which is used for acquisition of a blood vessel image of a desired region of the object, with a second sequence portion for measuring a second echo signal, which is used for acquisition of the blood flow information of the object. Then, by acquiring the blood flow information of the object using the second echo signal and processing an image, which is reconstructed using the first echo signal, using the acquired blood flow information, at least one of the artery and the vein is extracted.

In addition, the present invention includes a body motion information detection unit that detects periodic body motion information of an object, and a plurality of cycle periods of periodic body motion is set as a repetition period of at least a part of the imaging sequence. In this case, the first and second sequence portions may be executed in different cycle periods or may be executed in the same cycle period. For example, an electrocardiograph is provided, and an examination scan, which repeats an imaging sequence at the time of electrocardiographic synchronization that is synchronized with the electrocardiogram of the object, is set. In this case, the first and second sequence portions are also repeated at the time of electrocardiographic synchronization. Specifically, the imaging sequence is repeated in synchronization with an electrocardiogram R wave of an object, and each of the first and second sequence portions starts after a predetermined waiting time from the R wave. In addition, the first and second sequence portions may be executed in different cardiac beat periods or may be executed in the same cardiac beat period.

The waiting time from the R wave is set according to the purpose of each of the first and second sequence portions. That is, execution periods of the first and second sequence portions are set to be different within one cardiac beat (R-R) period according to their purposes. Specifically, in order to draw blood vessel images of both an artery and a vein with high brightness and high image quality, it is preferable that an echo signal be measured in a stable period in which the blood flow speed is low. Therefore, the execution of the first sequence portion whose purpose is to acquire a blood vessel image of a desired region of an object is set in diastole. On the other hand, in order to acquire the blood flow information by which an artery and a vein can be easily identified, it is preferable to use a speed difference between the artery and the vein. Therefore, the execution of the second sequence portion whose purpose is to acquire the blood flow information of an object is set in systole.

In order to execute the first sequence portion in diastole, it is necessary to set the waiting time TD1 until the start of the first sequence portion from an R wave. Similarly, in order to execute the second sequence portion in systole, it is necessary to set the waiting time TD2 until the start of the second sequence portion from an R wave. Periods of systole and diastole in the R-R interval can be approximately determined according to the R-R interval. In the present invention, therefore, a preparatory scan for adjusting TD1 and TD2 is not required basically. It is possible to set these waiting times on the basis of an interval between R waves from the electrocardiogram and pulse wave monitor 27.

In addition, although the present invention assumes that a blood vessel image is captured without using a contrast medium, it is also possible to perform the same processing when using a contrast medium.

Specific Content of the First Embodiment

Hereinafter, an MRI apparatus and a blood vessel image capturing method of the first embodiment will be described in detail.

In this first embodiment, first and second sequence portions which form an imaging sequence are executed in different cardiac beat periods. Hereinafter, the present embodiment will be described in detail using the accompanying drawings.

(Regarding an Imaging Sequence)

First, an imaging sequence related to the first embodiment will be described. In the first embodiment, an examination scan which repeats an imaging sequence at the time of electrocardiographic synchronization with a plurality of cardiac beat periods as one repetition time is set. However, the repetition time does not need to be set as the same heart rate in all iterations of the imaging sequence, and the repetition time may be changed during an examination scan according to the imaging conditions, desired image quality, and the like.

In addition, electrocardiographic synchronization, in which a first sequence portion is executed in diastole of one cardiac beat period of a plurality of cardiac beat periods and a second sequence portion is executed in systole of a different cardiac beat period from the first sequence portion, is assumed.

FIG. 2(a) is a timing chart showing an example of the imaging sequence related to the present embodiment. In the imaging sequence shown in FIG. 2(a), three cardiac beats are set as one repetition time, a sequence based on the FSE method (hereinafter, referred to as an FSE method sequence) is executed as a first sequence portion 201, and a sequence based on the PC method (hereinafter, referred to as a PC method sequence) is executed as a second sequence portion 202. (hereinafter, the first sequence portion 201 is also called the FSE method sequence 201. Similarly, the second sequence portion 202 is also called the PC method sequence 202.) All of these FSE method and PC method are known different imaging methods, and the specific content of the sequences will be described later. In addition, one repetition time may be two cardiac beats or four cardiac beats or more. In addition, the FSE method sequence 201 which is a first sequence portion starts after the waiting time TD1 from a first R wave 203, so that the FSE method sequence 201 is executed in diastole of a first cardiac beat period 221 of the three cardiac beat periods. The PC method sequence 202 which is a second sequence portion starts after the waiting time TD2 from a second R wave 204, so that the PC method sequence 202 is executed in systole of a second cardiac beat period 222 of the three cardiac beat periods. A third cardiac beat period 223 is set as a magnetization recovery period for which nothing is executed.

Next, an imaging region of each of the sequence portions 201 and 202 will be described. In order to acquire a blood vessel image of a desired region of an object, the first sequence portion 201 sets a wide region including the desired region as an imaging region. For example, a three-dimensional region including a desired blood vessel (an artery or a vein) can beset as an imaging region. This three-dimensional region is imaged in a three-dimensional manner, thereby acquiring a three-dimensional image. On the other hand, in order to acquire the blood flow information, the second sequence portion 202 sets a region including a desired blood vessel in a region inside or near the imaging region of the first sequence portion 201. In this case, the imaging sections may be made different by making the imaging region of the second sequence portion narrower than the imaging region of the first sequence portion, so that a three-dimensional image acquired in the first sequence portion is not unnecessarily influenced.

As an example, FIG. 2(b) shows an imaging region when capturing a blood vessel image of a leg. In FIG. 2(b), an imaging region (FOV) 211 of the FSE method sequence 201 which is the first sequence portion is shown by the solid line, and an imaging region (FOV) 212 of the PC method sequence 202 which is the second sequence portion is shown by the broken line. The imaging region 211 of the FSE method sequence 201 shows an example when 3D imaging of the coronal (COR) plane is executed, and the imaging region 212 of the PC method sequence 202 shows an example when 2D imaging of the axial (AX) plane is executed. The imaging region 212 of the PC method sequence 202 is within the three-dimensional imaging region 211 of the FSE method sequence 201, includes an artery or a vein, and is a two-dimensional sectional region with a thickness of about 10 mm which is approximately perpendicular to the traveling direction of the artery or the vein. In this manner, blood flow information regarding the artery and the vein can be acquired by the PC method sequence 202, and an influence of the imaging region 211 on a blood vessel image caused by the execution of the PC method sequence 202 can be reduced to the extent that is substantially negligible.

Next, advantages when an imaging sequence obtained by combining the first and second sequence portions 201 and 202 is executed as one same examination scan will be described. In the present embodiment, blood flow information is acquired on the basis of an echo signal (second echo signal) measured in the second sequence portion 202, and at least one of an artery and a vein is separated in a blood vessel image, which is acquired from an echo signal (first echo signal) measured in the first sequence portion 201, using the blood flow information. In order to perform this separation process with high accuracy, it is important that there is no positional deviation between the blood flow information and a blood vessel image. For this reason, the examination scan of the present embodiment is preferable in which the first and second sequence portions 201 and 202 are alternately executed and outputs from the respective sequence portions 201 and 202 can be simultaneously acquired.

Specifically, as will be described later, in the present embodiment, the blood flow information acquired by the second sequence portion 202 is an image which enables both identifying the blood vessel type and detecting the blood vessel position. By applying an image processing technique to the blood vessel image obtained by the first sequence portion 201 using the position of an artery or a vein detected from this image as a starting point, at least one of the artery and the vein is separated. In order to perform these processes with high accuracy, it is important that there is no positional deviation between an image of the second sequence portion 202 and an image of the first sequence portion 201 and the origin specified by the image of the second sequence portion 202 is disposed on the blood vessel of the image of the first sequence portion 201. For this reason, the examination scan shown in FIG. 2(a) is preferable in which the first and second sequence portions 201 and 202 are alternately executed and both outputs are simultaneously generated.

(Specific Example of the FSE Method Sequence)

The FSE method which is the basis of the FSE method sequence 201 of the present embodiment is a known technique, and a sequence based on this known technique can be used as the FSE method sequence 201. For example, the sequence disclosed in FIG. 1 and the like of PTL 5 can be used. Detailed explanation of the FSE method sequence 201 will be omitted herein.

(Specific Example of the PC Method Sequence and its Image)

Figure 3:
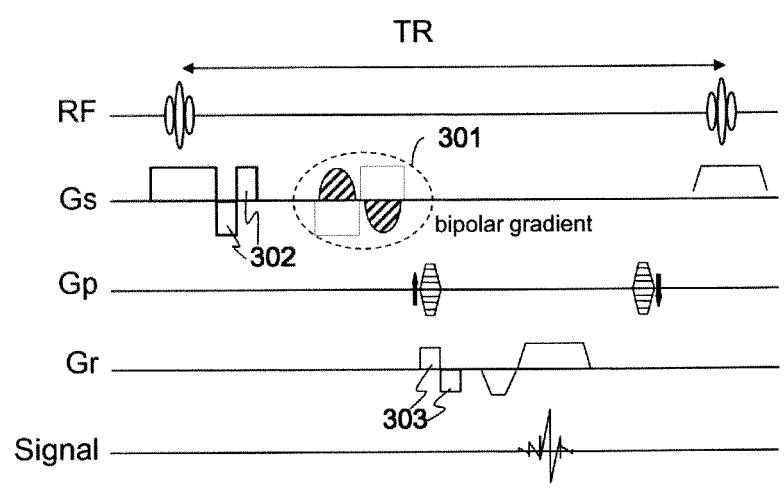
FIG. 3 is a sequence chart showing an example of a PC method sequence related to the first embodiment.

Next, the PC method will be described using an example of the PC method sequence 202 shown in FIG. 3.

The PC method sequence 202 is a sequence obtained by adding a pair of gradient magnetic field pulses with the opposite polarities and the same magnitude, that is, a bipolar gradient magnetic field pulse (hereinafter, referred to as a bipolar gradient) 301 to a normal sequence. A phase shift occurs only in the hydrogen atom which moves in the application direction of the bipolar gradient 301. Then, the bipolar gradient 301 is applied along the traveling direction of a desired blood vessel which needs to be drawn as a blood vessel image. In addition, a difference between echo signals, which have been measured by performing the PC method sequence 202 twice while inverting the polarity of the bipolar gradient 301, is calculated. In this manner, a signal of a stationary part is removed, and only a region where a phase shift has occurred can be imaged. As a result, it is possible to acquire a desired blood vessel image. In order to draw blood vessels traveling in a plurality of directions, it is preferable to add the bipolar gradient 301 in each direction.

When imaging the leg region shown in FIG. 2(b), it is necessary to apply the bipolar gradient 301 in an H-F direction since the main blood vessels travel in a direction from the head to the feet (H-F direction). The PC method sequence 202 shown in FIG. 3 is a known gradient echo method sequence, and the H-F direction is a slice direction. Accordingly, the bipolar gradient 301 is added as a part of a slice direction gradient magnetic field. This causes a phase shift only in the hydrogen atom which flows in the slice direction. Only the blood flow which flows in the slice direction is imaged using a difference between echo signals measured by executing the sequence 202 in FIG. 3 and the sequence 202 in FIG. 3 which is obtained by inverting only the polarity of the bipolar gradient 301. In addition, known flow compensation gradient magnetic field pulses 302 and 303 for compensating for (rephrasing) the phase dispersion caused by the blood flow is added in each direction to the PC method sequence 202 in FIG. 3.

The amount of phase shift caused by the bipolar gradient 301 is proportional to the blood flow speed in a direction of the applied bipolar gradient 301. In addition, since the direction of blood flow can be estimated by noting the positive or negative sign of the amount of phase shift, it is possible to identify which one of blood vessels traveling in parallel in the same direction is at the upstream side or the downstream side. For example, a blood flow in a direction from the heart to the feet or a blood flow from the feet to the heart can be estimated.

In addition, it is also possible to set the blood flow speed of interest by adjusting the amount of application of the bipolar gradient 301. The blood flow speed of interest is generally called speed encode (hereinafter, referred to as $V_{enc}$). The relationship among the blood flow speed V, the $V_{enc}$ value, and the amount of phase shift $\phi$ is as follows.

$$\Phi = \gamma \cdot (V_{enc} \text{value}) \cdot V \quad (1)$$

In this case, the $V_{enc}$ value is set according to the blood flow speed V such that $|\phi| < \pi/2$ is satisfied. For example, when an artery and a vein of a leg are assumed, the blood flow speed of the artery is about 30 to 70 cm/s and the blood flow speed of the vein is about 10 cm/s. Accordingly, the allowable $V_{enc}$ value is 30 to 50 cm/s.

Thus, since the PC method allows identifying the speed and direction of blood flow, it is possible to identify an artery and a vein using the blood flow speed and the direction as indices. In particular, according to the PC method, peripheral artery and vein with low blood flow speed can be identified using the information regarding the blood flow direction. Therefore, the PC method is useful in terms of improvements in separability of an artery and a vein. In addition, in order to improve the separability of an artery and a vein, it is preferable to measure an echo signal by the PC method sequence 202 in systole when the blood flow speed of an artery becomes maximum and a blood flow speed difference between the artery and the vein becomes maximum accordingly.

In addition, using the PC method sequence 202 that allows identifying the speed and direction of blood flow is a great advantage compared with known techniques. That is, in the techniques of PTL 1 to PTL 4 described in the related art, when applying a gradient magnetic field pulse for phase dispersion in order to disperse the phase of an artery with high blood flow speed in systole, it is possible to select the application direction of the gradient magnetic field pulse corresponding to the traveling direction of a blood vessel. However, in the case of blood vessels traveling in parallel in the same direction, it is not possible to distinguish which one of the blood vessels is an upstream or a downstream and to apply a gradient magnetic field pulse to only an artery. As a specific example, a case is assumed in which a gradient magnetic field pulse for phase dispersion is applied to an artery, which flows from the heart to the feet, and a vein, which flows from the feet to the heart, in the body axis direction. When the blood flow speed of the artery is almost equal to the blood flow speed of the vein, the signal strengths of both the blood vessels are reduced to the same extent by application of the gradient magnetic field pulse for phase dispersion. In the related art, the artery and the vein are separated from each other using the fact that the blood flow speed of the artery is high and accordingly the signal strength is suppressed. For this reason, in the case of a peripheral part where the blood flow speed of the artery is low, the separability of an artery and a vein is reduced.

In contrast, in the present embodiment using the PC method, it is possible to acquire the information regarding the speed and direction of blood flow as described above. Therefore, it is possible to identify an artery and a vein using this information as an index. In particular, peripheral artery and vein with low blood flow speed can be identified using the information regarding the blood flow direction. Therefore, the present embodiment is useful in terms of improvements in separability of an artery and a vein.

(Entire Process Flow)

Figure 4:
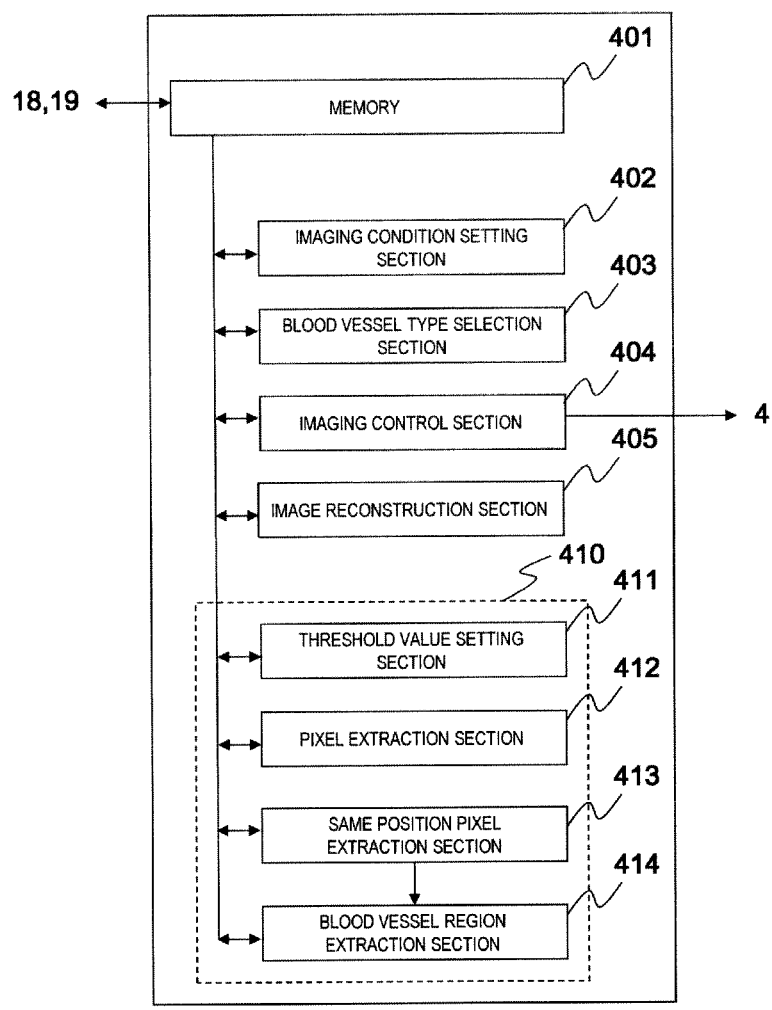
FIG. 4 is a view showing a functional block diagram of a CPU 8 related to the first embodiment.
Figure 5:
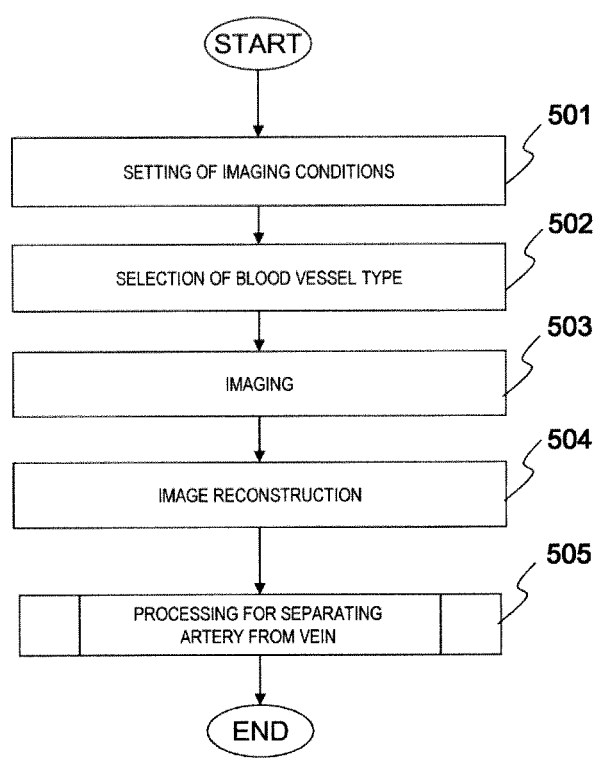
FIG. 5 is a flow chart showing the entire process flow related to the first embodiment.

Next, performing an examination scan using the above-described imaging sequence and reconstructing a blood vessel image using a measured echo signal, the device configuration for separating an artery from a vein on the reconstructed blood vessel image, and the process flow will be described on the basis of FIGS. 4 and 5. FIG. 4 shows a functional block diagram of the CPU 8, and FIG. 5 is a flow chart showing the entire process flow of the present embodiment. As shown in FIG. 4, the CPU 8 includes a memory 401, an imaging condition setting section 402 which sets imaging conditions, a blood vessel type selection section 403 which selects the type of a blood vessel to be drawn, an imaging control section 404 which sets an imaging sequence specifically, an image reconstruction section 405 which reconstructs an image using an echo signal, and a processing section group 410 which is shown by a dotted frame and performs processing for separating an artery from a vein. The detailed configuration of the processing section group 410 will be described later.

In step 501, the imaging condition setting section 402 displays a screen for setting the imaging conditions on the display 20 and receives an operator's setting input. For example, the imaging condition setting section 402 displays a positioning image and the like, which have been imaged in advance, on the display 20. The operator sets a first ROI as the imaging region (FOV) 211 of the FSE method sequence 201 and a second ROI as the imaging region (FOV) 212 of the PC method sequence 202 on the positioning image using the track ball or mouse 23. In addition, the operator sets the imaging conditions (TR, TE, TD1, TD2, and the like) of the respective sequences 201 and 202. In addition, TD1 and TD2 may also be set as constants set in advance instead of receiving the setting from the operator. When capturing a blood vessel image of the leg region, it is preferable to adopt 3D imaging of the coronal plane in the FSE method sequence 201 and 2D imaging of the axial (AX) plane with a small slice thickness in the PC method sequence 202 as described above.

In step 502, the blood vessel type selection section receives the selection of the type of a blood vessel to be extracted. For example, the blood vessel type selection section displays a menu on the display 20 so that the type of a blood vessel to be extracted from an artery and a vein can be selected, and receives an operator's selection. The operator selects either or both of the artery and the vein. In addition, the CPU 8 stores the information of the selected blood vessel type in the memory 401.

In step 503, the imaging control section 404 sets an imaging sequence, which is configured to include the FSE method sequence 201 and the PC method sequence 202, specifically on the basis of the imaging conditions set and input by the operator in step 501, and notifies the sequencer 4 of the specific configuration data to instruct the sequencer 4 to start an examination scan. The sequencer 4 starts an examination scan on the basis of the notified specific configuration data, detects electrocardiographic waveforms (R waves 203 and 204 and the like) from the object and repeats the imaging sequence at the time of electrocardiographic synchronization, and controls measurement of an echo signal based on the FSE method sequence 201 and an echo signal based on the PC method sequence 202.

In step 504, the image reconstruction section 405 reconstructs an image using each echo signal measured in step 503. That is, the image reconstruction section 405 reconstructs an FSE image of the first ROI 211 using the echo signal based on the FSE method sequence 201 and reconstructs a PC image of the second ROI 212 using the echo signal based on the PC method sequence 202. This PC image is an image including the blood flow information of the blood vessel included in the FSE image.

In step 505, the processing group 410 performs processing for separating an artery from a vein in the FSE image using the PC image and the FSE image. As a result, a blood vessel image showing the blood vessel type selected in step 502 is acquired. The acquired blood vessel image is displayed on the display 20, and the blood vessel image data is stored in the magnetic disk 18. The above is an explanation regarding the entire process flow of the present embodiment.

(Regarding Image Processing for Separation of an Artery and a Vein)

Details of the processing for separating an artery from a vein by the processing group 410 in the above step 505 will be described. As shown in FIG. 4, the processing group 410 for processing for separating an artery from a vein includes a threshold value setting section 411, a pixel extraction section 412, a same position pixel extraction section 413, and a blood vessel region extraction section 414.

Figure 6:
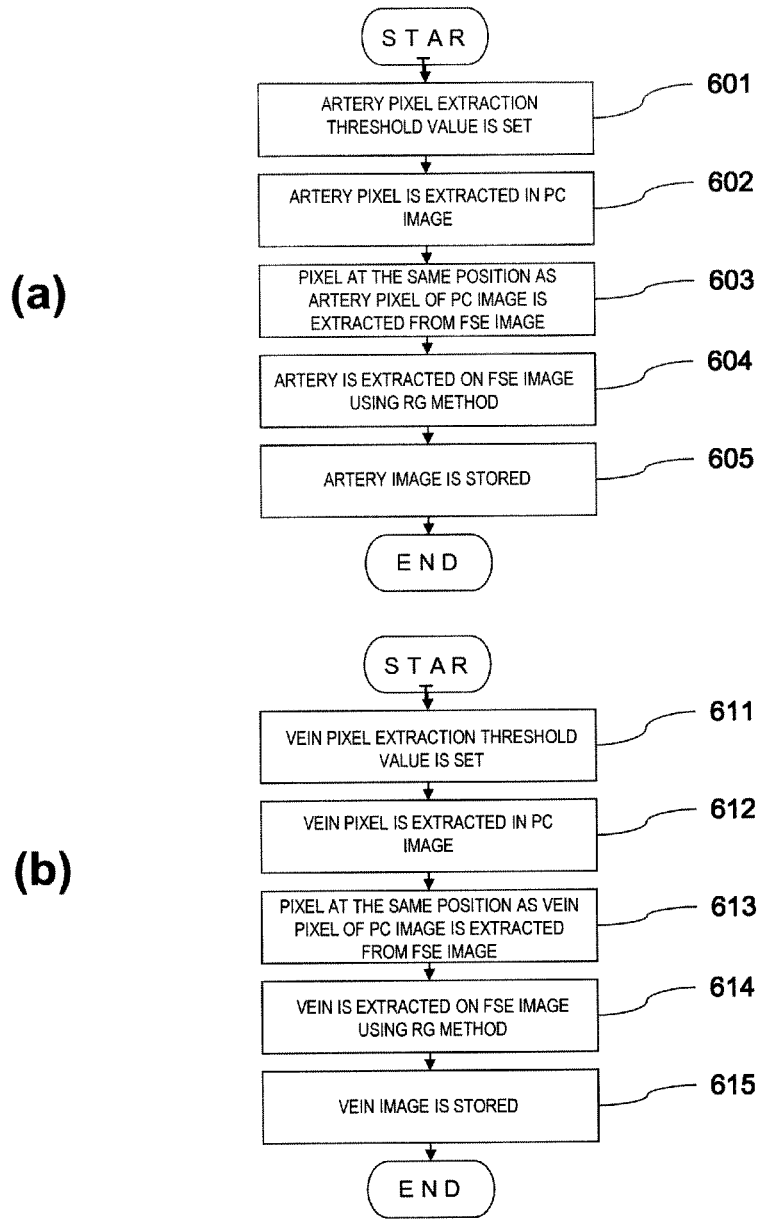
FIG. 6 is a flow chart showing the flow of processing for separation of an artery and a vein related to the first embodiment, where

The flow chart of FIG. 6 is a process flow of separating an artery from a vein in step 505 of the present embodiment, which is performed by cooperation of the respective functional sections of the CPU 8 including the processing group 410. FIG. 6(a) shows the process flow when extracting an artery, and FIG. 6(b) shows the process flow when extracting a vein. A program for realizing the processes of the flow charts of FIGS. 6(a) and 6(b) is stored in the magnetic disk 18 in advance. This program is loaded to the CPU 8 and executed as necessary in order to execute the processing for separating an artery from a vein.

The threshold value setting section 411 sets an artery pixel extraction threshold value and a vein pixel extraction threshold value that are used in steps 601 and 611 of the processing for separating an artery from a vein in FIGS. 6(a) and 6(b). These threshold values are values for extracting pixels of a desired blood vessel type in a PC image. These threshold values may be set by reading the values stored in the magnetic disk 18 in advance, or it is possible to display a threshold value input screen on the display 20 and set the values input and set by the operator as the threshold values. As described above, the signal strength of the PC image corresponds to the blood flow speed. Accordingly, the artery pixel extraction threshold value is set to be high in order to extract an artery pixel with high blood flow speed and the vein pixel extraction threshold value is set to be low in order to extract a vein pixel with low blood flow speed. For example, when a pixel with a blood flow speed of 20 cm/s or more is extracted as an artery and a pixel with a blood flow speed of −5 to −15 cm/s is extracted as a vein, these values are set as threshold values. Here, the sign of the blood flow speed of a component that flows from the heart to the feet is positive. For the artery pixel extraction threshold value, it is more preferable to change the threshold value of the blood flow speed for each imaging part, such as a thigh, a knee, or the vicinity of an ankle, or so as to correspond to $V_{enc}$ set at the time of PC method imaging.

In steps 602 and 612, the pixel extraction section 412 compares each pixel value of the PC image with the threshold value using the threshold values set by the threshold value setting section 411 and extracts a pixel with a pixel value, which is equal to or greater than the artery pixel extraction threshold value, when extracting an artery pixel and extracts a pixel with a pixel value, which is equal to or less than the vein pixel extraction threshold value or which is between a plurality of vein pixel extraction threshold values, when extracting a vein pixel. In addition, the positional information of each extracted pixel on the image is stored in the memory 401.

In steps 603 and 613, the same position pixel extraction section 413 extracts the pixel position on the FSE image which corresponds to the positional information of a pixel extracted on the PC image by the pixel extraction section 412. An image captured by a normal MRI apparatus is stored including the information such as the imaging conditions based on DICOM. By using the information, it is possible to calculate in which position (for example, 25 mm in the right direction, 10 mm in the depth direction, and 3 mm upward from the center of the magnetic field) of imaging space each slice surface has been imaged. In addition, since the pixel size, slice thickness, and the like are known by the imaging conditions, it is possible to check to which pixel on an image an arbitrary region in imaging space corresponds. Since this matching does not depend on the imaging sequence, processing for extracting the pixel position on the FSE image corresponding to the pixel position extracted on the PC image is easy. Thus, the same position pixel extraction section 413 extracts the pixel position on the FSE image, which corresponds to the pixel position extracted on the PC image, on the basis of the imaging conditions of the PC image and the imaging conditions of the FSE image.

Alternatively, an operator may designate and input the pixel position of an artery or a vein directly on the FSE image. In this case, the same position pixel extraction section 413 extracts the pixel position that the operator has designated on the FSE screen through the track ball or mouse 23.

In addition, the same position pixel extraction section 413 stores in a memory the positional information of the pixel extracted on the FSE image as described above.

In steps 604 and 614, the blood vessel region extraction section 414 sets the pixel position on the FSE image extracted by the same position pixel extraction section 413 as an origin (starting point) and repeats processing for extending a region sequentially from the starting point using a known region growing (hereinafter, referred to as RG) method, thereby extracting an artery or a vein on the FSE image. The blood vessel region extraction section 414 displays a region extension result including the progress of region extension on the display 20 as necessary. As a result, the operator can check whether region extension is performed appropriately as necessary. Then, in steps 605 and 615, a region extension processing result image is stored in the magnetic disk 18 as an artery image or a vein image.

In the above-described region extension processing, it is necessary to remove isolated points on the FSE image in order to remove the influence of noise and the like. That is, for one pixel having a pixel value equal to or greater than a predetermined threshold value, it is verified whether the pixel value of an adjacent pixel, which is adjacent to the one pixel, is also equal to or greater than the threshold value. When there is no adjacent pixel having a pixel value equal to or greater than the threshold value, the one pixel is deleted. Alternatively, it is also possible to calculate the area of a region, which includes one pixel having a pixel value equal to or greater than a predetermined threshold value and its adjacent pixels, and to delete the one pixel when the area is less than a predetermined threshold value, thereby removing the influence of noise. In addition, since a blood vessel image generally has a wide signal strength range, region extension may be interrupted or protruding to a region other than the blood vessel may occur during the execution of region extension processing. In order to prevent this, threshold value setting not to extend a region too much, processing for reducing a region when the region has been extended too much, and the like are performed. As methods of performing the above-described threshold value setting and the like easily, a method of changing automatically the conditions of region extension dynamically according to the position or brightness of a blood vessel, a function of removing the protrusion occurring in the course of extension automatically by interactive operation, and the like are under development. These are common techniques in the RG method.

The CPU 8 executes either or both of the artery extraction process shown in FIG. 6(*a*) and the vein extraction process shown in FIG. 6(*b*) according to the blood vessel type selected in the above step 502. When both the artery extraction process and the vein extraction process are executed, any one of them may be executed first. The process flow when extracting a vein in FIG. 6(*a*) will be described.

In step 601, the threshold value setting section 411 sets an artery pixel extraction threshold value for extracting an artery pixel in the PC image. As the setting method, as described above, the threshold value stored in the magnetic disk 18 in advance may be read and set, or the threshold value input and set by the operator may be set.

In step 602, the pixel extraction section 412 compares the artery pixel extraction threshold value set in step 601 with each pixel value of the PC image and extracts a pixel, which has a pixel value equal to or greater than the artery pixel extraction threshold value, in the PC image.

In step 603, the same position pixel extraction section 413 extracts a pixel at the same position as the artery pixel, which has been extracted on the PC image in step 602, from the FSE image.

In step 604, the blood vessel region extraction section 414 sets the pixel position on the FSE image extracted in step 603 as a starting point and repeats processing for extending a region sequentially from the starting point using the RG method, thereby extracting an artery on the FSE image. In this case, the blood vessel region extraction section 414 displays a region extension processing result including the progress on the display 20.

In step 605, the blood vessel region extraction section 414 stores a region extension processing result image in the magnetic disk 18 as an artery image. The above is an explanation regarding the process flow of extracting an artery from the FSE image.

Next, the vein extraction process in FIG. 6(*b*) will be described. Since the vein extraction process is similarly performed by changing an "artery" into a "vein" in the above artery extraction process, only the outline will be described.

In step 611, the threshold value setting section 411 sets a vein pixel extraction threshold value.

In step 612, the pixel extraction section 412 extracts a pixel, which has a pixel value equal to or less than the vein pixel extraction threshold value or a pixel value in a range of the vein pixel extraction threshold value, in the PC image.

In step 613, the same position pixel extraction section 413 extracts a pixel at the same position as the vein pixel, which has been extracted on the PC image, from the FSE image.

In step 614, the blood vessel region extraction section 414 extracts a vein on the FSE image and displays a region extension processing result including the progress on the display 20.

In step 615, the blood vessel region extraction section 414 stores a region extension processing result image in the magnetic disk 18 as a vein image. The above is an explanation regarding the process flow of extracting a vein from the FSE image.

As described above, in the MRI apparatus and the blood vessel image capturing method of the present embodiment, a plurality of images (an FSE image and a PC image) with different characteristics are captured by one examination scan using different imaging methods (a PC method and an FSE method), and an artery and a vein are separated from each other on the image (FSE image) acquired by the other imaging method (FSE method) using the blood flow information, which is extracted by the one imaging method (PC method), by post-processing (starting point extraction and the RG method) using the plurality of images with different characteristics. Then, unlike the related art, the user does not need to see an image obtained by performing a preparatory scan, select systole and diastole, and determine DT or AT of the FSE sequence on the basis of this. As a result, an artery image or a vein image can be generated objectively from the blood flow information acquired by the PC method. Therefore, according to an object or an imaging part, an artery image or a vein image can be acquired with high accuracy. In addition, since a user does not need to select a systolic or diastolic image, it is possible to reduce the burden on the user.

In addition, by using the PC method, an artery and a vein with no significant difference in the blood flow speed, such as peripheral parts of an object, can be identified from the blood flow direction. Therefore, also for the peripheral part, it is possible to acquire an artery image or a vein image with high accuracy.

In addition, in the related art, since an artery image is obtained by removing a vein image by weighting difference of two images, it is necessary to set an appropriate weighting coefficient by trial and error or the like. In the present embodiment, however, it is not necessary to calculate a difference image. For this reason, since it is not necessary to set the weighting coefficient by trial and error or the like, an artery image and a vein image can be separated from each other with high accuracy.

In addition, although a preparatory scan, an FSE sequence of diastole, and an FSE sequence of systole need to be executed in the related art, it is necessary to perform only the FSE method sequence 201 of diastole and the PC method sequence 202 of systole in the present embodiment. Accordingly, examination time is shortened compared to that in the related art, a blood vessel image in which an artery and a vein are separated with high accuracy can be acquired. As a result, it is possible to improve the separability of an artery and a vein.

In addition, since the FSE method sequence 201 and the PC method sequence 202 are executed by one examination scan, there is also an effect that this is less susceptible to the influence of the positional deviation due to body motion.

Second Embodiment

Next, an MRI apparatus and a blood vessel image capturing method of a second embodiment of the present invention will be described. In the first embodiment described above, the first and second sequence portions 201 and 202 are executed in the first and second cardiac beats 221 and 222, respectively. In the second embodiment, however, the first and second sequence portions 201 and 202 are executed in the same cardiac beat period as shown in the timing chart of FIG. 7. Hereinafter, the present embodiment will be described in detail with reference to the accompanying drawings using an example of the case where the FSE method sequence is used as the first sequence portion 201 and the PC method sequence 202 is used as the second sequence portion.

Also in the second embodiment, similar to the first embodiment, an imaging sequence is repeated at the time of electrocardiographic synchronization with a plurality of cardiac beat periods as one repetition time. Electrocardiographic synchronization, in which the first sequence portion 201 is executed in diastole of one cardiac beat period of a plurality of cardiac beat periods and the second sequence portion 202 is executed in systole of the same cardiac beat period as the first sequence portion 201, is assumed. As a result, within one repetition of the imaging sequence, the second sequence portion 202 is first executed and then the first sequence portion 201 is executed. However, the repetition time does not need to be set as the same heart rate in all iterations of the imaging sequence, and the repetition time may be changed during an examination scan according to the imaging conditions, desired image quality, and the like.

Figure 7:
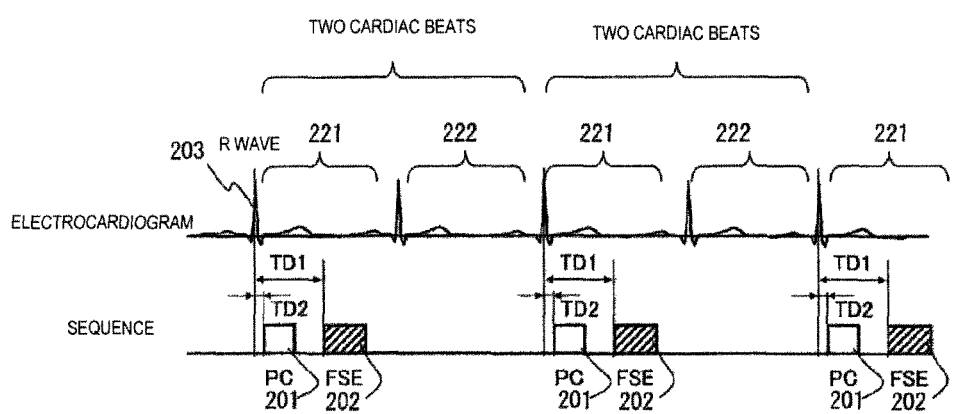
FIG. 7 is a view showing a timing chart of an imaging sequence related to a second embodiment.

In the example shown in FIG. 7, two cardiac beats 221 and 222 are set as one repetition time of the imaging sequence. In addition, one repetition time may be three cardiac beats or more. In addition, the FSE method sequence which is the first sequence portion 201 starts after waiting time TD1 from a first R wave, so that the FSE method sequence is executed in diastole of the first cardiac beat period 221 of the two cardiac beat periods. The PC method sequence which is the second sequence portion 202 starts after waiting time TD2 from the first R wave, so that the PC method sequence is executed in systole of the first cardiac beat period 221. The second cardiac beat period 222 is set as a magnetization recovery period for which nothing is executed.

Such an imaging sequence of the present embodiment is effective for the low heart rate, that is, along cardiac cycle.

Since processing other than the above imaging sequence is the same as that in the first embodiment, an explanation thereof will be omitted.

As described above, since the first and second sequence portions 201 and 202 are executed in the same cardiac beat period in the MRI apparatus and the blood vessel image capturing method of the second embodiment, it is possible to shorten the imaging time. This is particularly effective when one cardiac cycle of an object is long. Other effects are the same as those in the first embodiment.

Third Embodiment

Next, an MRI apparatus and a blood vessel image capturing method of a third embodiment of the present invention will be described. In the present embodiment, only the blood flow which flows in one direction is selectively identified using a sequence with pre-saturation based on a TOF (Time-Of-Flight) method (hereinafter, referred to as a TOF method sequence) as the second sequence portion 202 for measuring an echo signal used for acquisition of the blood flow information of the object. Hereinafter, the third embodiment will be described in detail.

(Regarding an Imaging Sequence)

First, an imaging sequence related to the present embodiment will be described. An imaging sequence of the third embodiment is also configured to include the first and second sequence portions 201 and 202, similar to the imaging sequence shown in FIG. 2 in the first embodiment. A TOF method sequence is used as the second sequence portion 202. That is, in the imaging sequence of the first embodiment shown in FIG. 2, the PC method sequence which is the second sequence portion 202 is replaced with the TOF method sequence, and the TOF method sequence is executed in a different cardiac beat period from the first sequence portion 201. Alternatively, it is also possible to adopt a configuration in which the PC method sequence which is the second sequence portion 202 is replaced with the TOF method sequence in the imaging sequence of the second embodiment shown in FIG. 7 and the TOF method sequence is executed in the same cardiac beat period as the first sequence portion 201. In any case, the TOF method sequence is executed in systole. Since matters other than these are the same as those in the first or second embodiment, a detailed explanation thereof will be omitted. Hereinafter, details of the TOF method sequence will be described.

Figure 8:
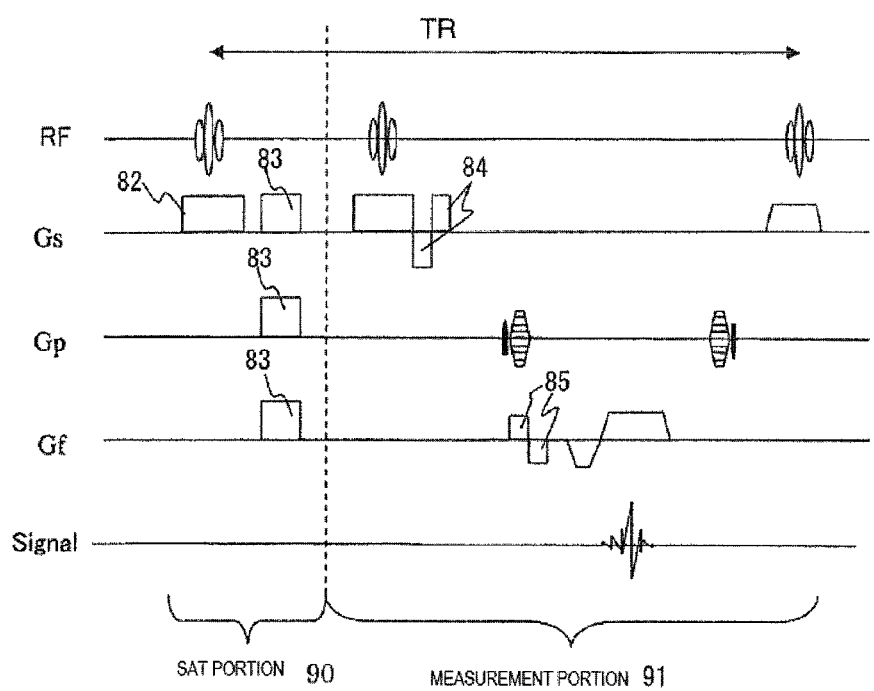
FIG. 8 is a sequence chart showing an example of a TOF method sequence related to a third embodiment.

FIG. 8 shows an example of the TOF method sequence. The TOF method sequence has a pre-saturation (SAT) portion 90 in the first half and a measurement portion 91 in the second half. The SAT portion 90 excites a desired pre-saturation region with an RF pulse 31 and a slice selection gradient magnetic field 82, and disperses the phase of the hydrogen atom in the excitation region with subsequent spoiler gradient magnetic field pulses 83a, 83b, and 83c in three axial directions. In this manner, it is possible to suppress a signal from the blood flow passing through the pre-saturation region. The measurement portion 91 in the second half is a normal sequence for measuring an echo signal from a region which is different from the pre-saturation region. The example shown in FIG. 8 is a known gradient echo method sequence in which known flow compensation gradient magnetic field pulses 84 and 85 are added.

(Regarding an Imaging Region)

Figure 9:
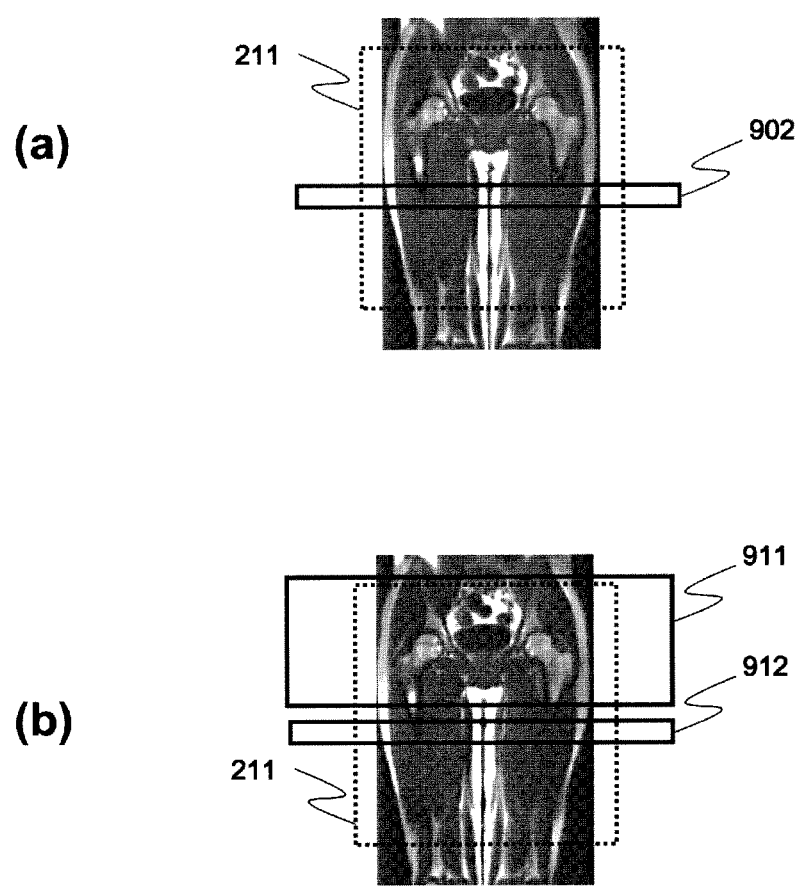
FIG. 9 is a view showing an example of an imaging region set when imaging the leg of an object using the TOF method sequence shown in FIG. 7, where

Next, an imaging region of the TOF method sequence is shown. This will be described using FIG. 9. FIG. 9 shows an example of an imaging region set when imaging the leg of an object using the TOF method sequence shown in FIG. 8. FIG. 9(a) shows an example of region setting when detecting an artery selectively, and FIG. 9(b) shows an example of region setting when detecting a vein selectively. Pre-saturation regions 901 and 911 to which pre-saturation pulses are applied by the SAT portion 90 are regions on one side in the blood flow direction which are adjacent to regions 902 and 912 imaged by the measurement portion 91 of the TOF method sequence.

As shown in FIGS. 9(a) and 9(b), regions adjacent to the imaging surface 211 of the first sequence portion 201 are set as the pre-saturation regions 901 and 911, and regions adjacent to the pre-saturation regions 901 and 911 are set as TOF method imaging regions 902 and 912. The TOF method imaging regions 902 and 912 are two-dimensional AX cross sections. Moreover, in the second sequence portion 202, pre-saturation pulses (gradient magnetic field pulses 83a, 83b, and 83c) are first applied to the pre-saturation regions 901 and 911 by the SAT portion 90, and then echo signals from the TOF method imaging regions 902 and 912 are measured by the measurement portion 91 of the TOF method sequence. Hydrogen atoms of the regions 901 and 911 to which pre-saturation pulses are applied are saturated to generate no more echo signals. As a result, in the TOF method imaging regions 902 and 912 adjacent to the pre-saturation regions 901 and 911, blood flows which flow from the opposite regions of the pre-saturation regions 901 and 911 to the TOF method imaging regions 902 and 912 are selectively imaged in the TOF image. In FIG. 9(a), the pre-saturation region 901 is set on the foot side of the TOF method imaging region 902. Accordingly, blood which moves from the heart to the feet and then flows to the TOF method imaging region 902, that is, an artery is selectively imaged.

On the other hand, in FIG. 9(b), the pre-saturation region 911 is set on the heart side of the TOF method imaging region 912. Accordingly, blood which moves from the feet to the heart and then flows to the TOF method imaging region 912, that is, a vein is selectively imaged. Using such a TOF image, the pixel position of an artery or a vein can be detected on the TOF image, as in the PC method. Then, by the same processing as in the first or second embodiment described above, region extension based on the RG method is performed with the pixel position on the same FSE image as the pixel position of the artery or the vein extracted on the TOF image as a starting point in the FSE image acquired in the first sequence portion 201. As a result, an artery or a vein can be selectively extracted on the FSE image.

Alternatively, each TOF image may be acquired in the second sequence portion 202 according to the presence or absence of the SAT portion 90 without changing the positions of the pre-saturation regions 901 and 911 and the positions of the TOF method imaging regions 902 and 912, and a blood vessel image of an artery or a vein may be acquired by arithmetic processing of these TOF images. When the SAT portion 90 is present, it is possible to acquire an image in which either the artery or the vein is drawn. When there is no SAT portion, it is possible to acquire an image in which both the artery and the vein are drawn. By operation of these two images, it is possible to acquire an image in which either or both of the artery and the vein are drawn.

As described above, in the MRI apparatus and the blood vessel image capturing method of the third embodiment, a TOF image is obtained by imaging a cross section approximately perpendicular to the blood flow by changing the relative positions of the pre-saturation regions 901 and 911 and the TOF imaging regions 902 and 912 according to the type of a blood vessel, which is to be suppressed, using the TOF method sequence as the second sequence portion 202. On the basis of the blood vessel pixel position extracted on this TOF image, a blood vessel image of an artery or a vein is acquired by the RG method on the image acquired in the first sequence portion 201. As a result, the same effects as in the first embodiment described above can also be obtained by the TOF method.

Fourth Embodiment

In the first to third embodiments described above, a plurality of continuous cardiac beat periods is set as a repetition time and the first sequence 201 and the second sequence are repeatedly executed alternately in diastole and systole. In this method, an arteriovenous image is captured from the first sequence 201, information of the speed or direction of the blood flow is acquired from the second sequence 202 and the information of the pixel position of an artery or a vein is acquired accordingly, and only an artery image or only a vein image is extracted from the arteriovenous image acquired in the first sequence 201 using the RG method with this pixel as a starting point.

In contrast, in a fourth embodiment, unlike the first to third embodiments, the second sequence (PC method sequence) 202 is first executed continuously over a plurality of cardiac beats for a plurality of cardiac time phases, thereby acquiring a blood flow information image for each cardiac time phase. That is, cine images of the blood flow information are obtained by the second sequence 202. Using the information acquired from the blood flow information cine images, DT and the like of the first sequence (FSE method sequence) 201 executed later are set. By executing the first sequence 201 on the basis of these, an image of only a vein and an image including an artery and a vein are acquired. Then, weighted differential processing on both the images is performed to separate only the artery image. Weighting coefficients used for the weighted differential processing are also set from the information acquired from the second sequence 202. Since it is important that there is no positional deviation between the blood flow information and a blood vessel image in order to execute this separation process with high accuracy, the examination scan which executes the PC method sequence 202 and the FSE method sequence 201 continuously is preferable.

Figure 10:
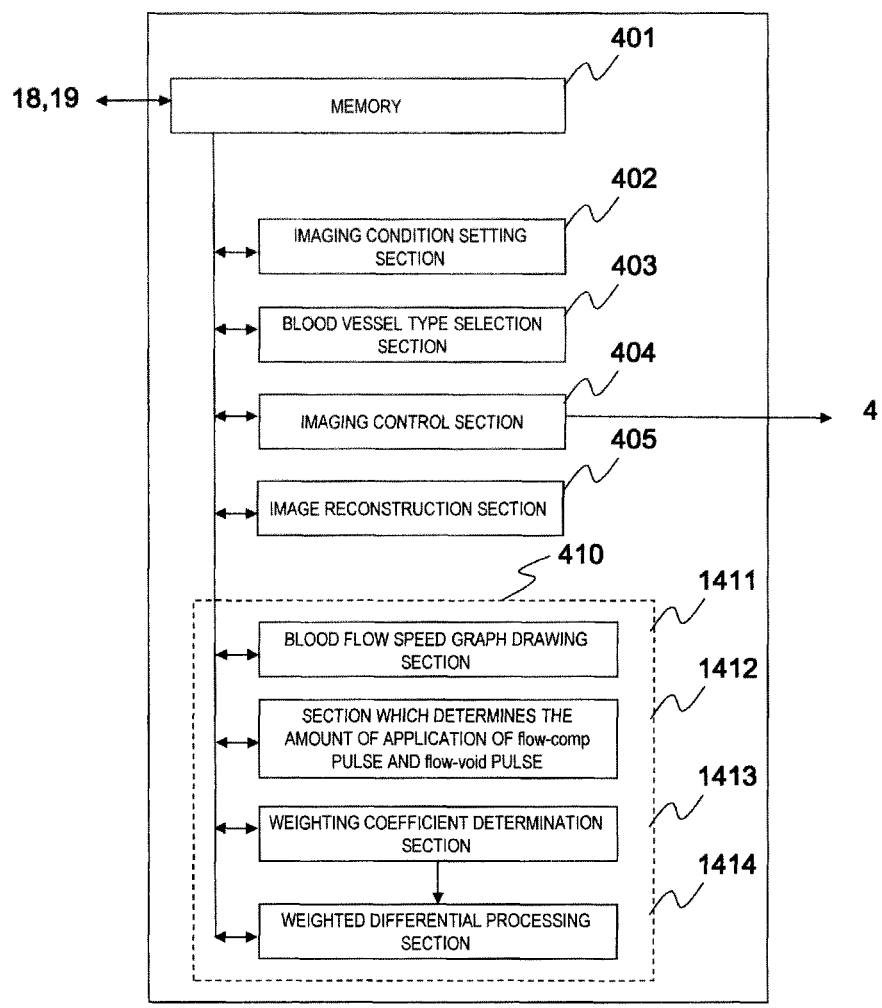
FIG. 10 is a functional block diagram of a CPU 8 related to a fourth embodiment.

Hereinafter, the MRI apparatus and the imaging sequence of the fourth embodiment will be specifically described using FIG. 10 and the like. The configuration of the MRI apparatus is the same as that in the first embodiment. FIG. 10 shows a functional block diagram of a CPU 8 in the fourth embodiment. An artery and vein separation processing group 410 includes a blood flow speed graph drawing section 1411, a section which determines the amount of application of a flow-void pulse and a flow-comp pulse of an FSE method sequence 1412, a weighting coefficient determination section 1413, and a weighted differential processing execution section 1414. Other configurations are the same as those shown in FIG. 4 in the first embodiment.

Figure 11:
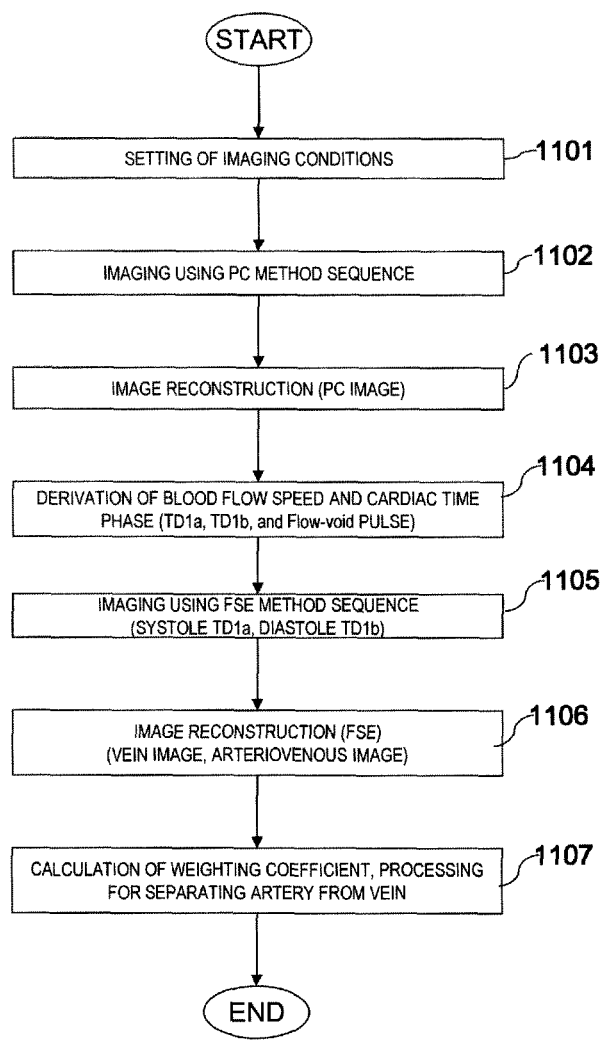
FIG. 11 is a flow chart showing the entire process flow of the fourth embodiment.

The flow of the process of capturing a blood vessel image of the fourth embodiment will be described using FIG. 11. First, in step 1102, the imaging condition setting section 402 receives from the operator a setting of imaging regions 211 and 212 or imaging conditions (TR, TE, and the like) of the first sequence (FSE method sequence) 201 and the second sequence (PC method sequence) 202, as in step 502 shown in FIG. 5 in the first embodiment. The imaging regions 211 and 212 are the same as those in the first embodiment. In addition, for TD1 of the FSE method sequence 201 among the imaging conditions, TD1a for systole and TD1b for diastole are determined by operation using an imaging result of the PC method sequence 203 as described below. Therefore, it is not necessary to request the operator to input TD1.

Figure 12:
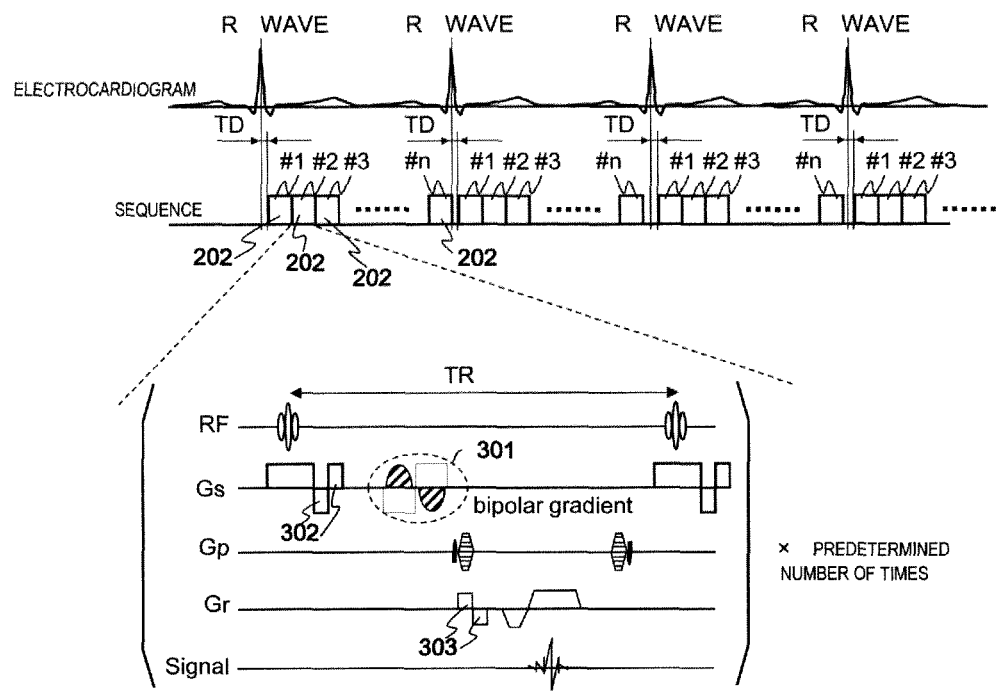
FIG. 12 is a sequence chart showing a PC method sequence of the imaging sequences related to the fourth embodiment.

Then, in step 1102, the imaging control section 404 executes capturing of a cine image using the PC method by setting the PC method sequence 202 in the sequencer 4 on the basis of the imaging conditions set in step 1101. The specific PC method sequence 202 is shown in FIG. 12. This is an imaging method of applying the bipolar gradient 301 along the traveling direction of a blood vessel, and is the same as the PC method sequence shown in FIG. 3 in the first embodiment. This PC method sequence 202 is repeated n times within one cardiac beat period 1202 after time TD2 elapses from an R wave 1201 from the object. This sequence is repeated over a plurality of cardiac beats for each of n cardiac time phases until an echo signal required to perform one image reconstruction is acquired. Then, the polarity of the bipolar gradient 301 is inverted to repeat similar operations.

In step 1103, the image reconstruction section 405 calculates a difference between echo signals, which have been measured by performing the PC method sequence 202 twice while inverting the polarity of the bipolar gradient 301 in step 1102, and performs image reconstruction for each of n cardiac time phases. Accordingly, a signal of a stationary part is removed. As a result, an image (blood vessel image) having a flow speed in the application direction of the bipolar gradient 301 as a value of a pixel can be acquired for each of n cardiac time phases. FIG. 13(a) shows an example of a PC image having a pelvic region as an imaging region. In this drawing, a region shown by the arrow is an artery.

Figure 14:
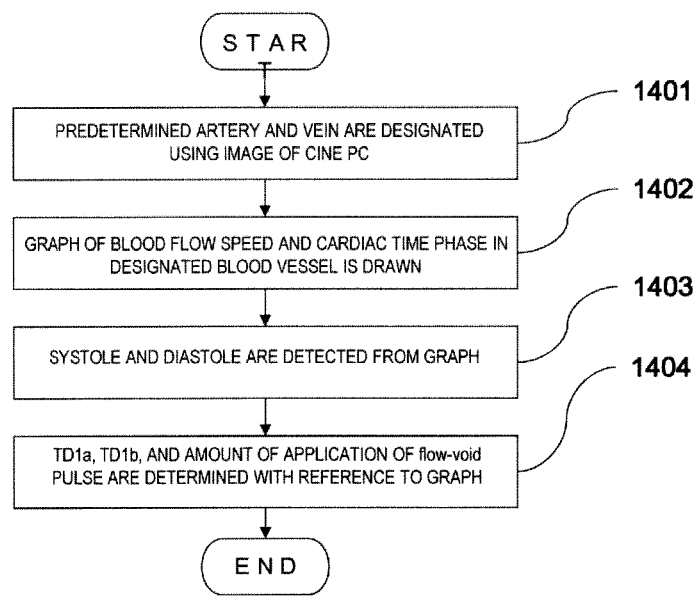
FIG. 14 is a flow chart showing step 1504 of the flow in FIG. 11 in detail.

Then, in step 1104, the blood flow speed graph drawing section 1411 derives the imaging conditions of the subsequent FSE method sequence 201 using the PC image acquired in the PC method sequence 202. In step 1103, a PC image is acquired for each of n cardiac time phases. When the PC image is two-dimensional image data, it becomes three-dimensional data by adding a time axis called a cardiac time phase further. Accordingly, in step 1401, a region of interest 1301 is set on the two-dimensional image data (PC image), and a graph of speed-time which has a blood flow speed on the vertical axis and elapsed time from an R wave on the horizontal axis can be created. FIG. 13(b) shows an example of the graph. Procedures of creating the graph and procedures of detecting systole and diastole from the graph and calculating the imaging conditions of the FSE method sequence and an example thereof are shown in the flow of FIG. 14. However, these are not limited to the procedures and the processing method shown in FIG. 14, and various methods may be applied as long as a graph can be created and the imaging conditions can be calculated by detecting systole and diastole from the graph and calculating each blood flow speed.

First, in step 1401, the blood flow speed graph drawing section 1411 cooperates with the imaging condition setting section 402 to receive operator's designation of the region of interest 1301 for an artery and the region of interest 1311 for a vein on the PC image. For example, the blood flow speed graph drawing section 1411 displays a PC image with one cardiac time phase shown in FIG. 13(a) on the display 20, and the operator designates the regions of interest 1301 and 1311 on the PC image using a device, such as the mouse 23.

In step 1402, the blood flow speed graph drawing section 1411 calculates a value of each pixel in the region of interest 1301 of an artery, that is, an average value of blood flow speed. Similarly, for PC images with the other (n−1) cardiac time phases, the average (average blood flow speed) of pixel values of pixels in the region of interest 1301 is calculated. An array having an average blood flow speed in the region of interest 1301 as a value of an element and the number of elements as the number of cardiac time phases n is created. Using this array, the graph of average blood flow speed and cardiac time phase time from an R wave) is created as shown in FIG. 13(b). In FIG. 13(b), the speed of a flow which flows in the direction from the head to the feet is shown by the negative value, and the opposite flow speed is shown by the positive value. On the other hand, values of pixels in the region of interest 1311 of a vein, that is, the average value of blood flow speed is calculated. Since the vein does not beat, it is not necessary to create a graph.

Then, in step 1403, processing for detecting systole and diastole is executed. Attention is paid to the characteristics of the blood flow speed in an artery that a difference between the blood flow speed in systole and the blood flow speed in diastole is large. In the array or graph, attention is paid to values (average blood flow speed) of the elements. Most simply, a maximum value 1302 and a minimum value 1303 of pixel values and a cardiac time phase which becomes the maximum value 1302 and a cardiac time phase which becomes the minimum value 1303 are calculated. Then, the region of interest 1301 where a difference between the maximum value 1302 and the minimum value 1303 is greater than a predetermined threshold value is determined to be the region of interest 1301 equivalent to an artery.

For the region of interest 1301 determined to be an artery, the maximum value 1302 and its cardiac time phase are the systolic blood flow speed and the systole (delay time TD1a from an R wave). In addition, the minimum value 1302 and its cardiac time phase are the diastolic blood flow speed and the diastole (delay time TD1b from an R wave). The calculated graph of blood flow speed and cardiac time phase shown in FIG. 13(b), delay time TD1a and TD1b of diastole and systole, systolic blood flow speed, diastolic blood flow speed, and blood flow speed of a vein are stored in the memory 401.

In step 1404, imaging parameters (TD1a, TD1b, Flow-void pulse 1504) used in the FSE method sequence are calculated. In the fourth embodiment, the FSE method sequence 201 is executed twice in systole and diastole, thereby acquiring a vein image and an arteriovenous image, respectively. When executing the FSE method sequence 201 in systole, it is necessary to execute the FSE method sequence 201 in predetermined delay time from an R wave for becoming systole. For this reason, TD1a calculated in step 1403 is set as the delay time TD1 for execution of the FSE method sequence 201 in systole. In addition, TD1b is similarly set as the delay time TD1 for execution of the FSE method sequence 201 of diastole.

Figure 15:
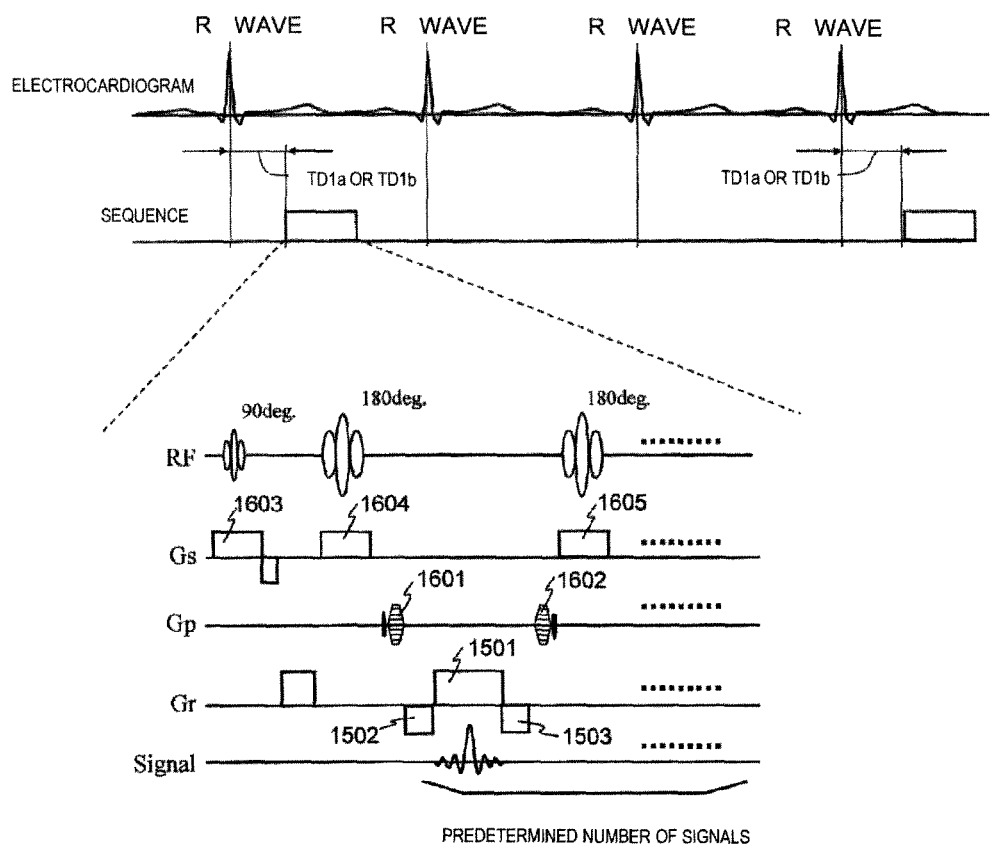
FIG. 15 is a sequence chart showing an FSE method sequence of the imaging sequences related to the fourth embodiment.

In addition, a known FSE sequence shown in FIG. 15 is used as the FSE method sequence executed in the fourth embodiment. When executing the FSE method sequence in systole (FIG. 16(b)) and also when executing the FSE method sequence in diastole (FIG. 16(a)), known flow compensation gradient magnetic field (hereinafter, referred to as Flow-comp) pulses 1502 and 1503 for compensating for (rephrasing) the phase dispersion caused by the blood flow are applied with the opposite polarity to a readout gradient magnetic field 1501 before and after the readout gradient magnetic field 1501. The amount of application of gradient magnetic field of the Flow-comp pulses 1502 and 1503 is determined such that the ratio of Flow-comp pulse 1502:readout gradient magnetic field 1501:Flow-comp pulse 1502=1:2:1 is satisfied with the amount of application of gradient magnetic field of the readout gradient magnetic field 1501 as a reference. In addition, since Flow-comp pulses 1502 and 1503 do not depend on the blood flow speed, Flow-comp pulses 1502 and 1503 may be set in advance instead of being derived in this step 1404.

Moreover, in the FSE method sequence 202 of systole, known gradient magnetic field (hereinafter, referred to as Flow-void) pulses 1504, 1505, and 1506 for dispersing the phase of arterial blood flow with high flow speed to weaken the signal strength are applied in respective axial directions of a signal readout gradient magnetic field direction Gr, a phase encoding direction Gp, and a slice direction Gs in addition to the above Flow-comp pulses 1502 and 1503. The amount of application of the Flow-void pulse 1504 in the Gr direction is determined corresponding to the systolic blood flow speed 1302 and the amount of application of the readout gradient magnetic field 1501. It is preferable to increase the amount of application of the Flow-void pulse 1504 as the blood flow speed decreases. Accordingly, for example, following Table 1 is stored in advance and the amount of application of the Flow-void pulse 1504 is determined with reference to the maximum blood flow speed 1302 and the table for each examination.

TABLE 1

| Blood flow speed in systole | Ratio of readout gradient magnetic field to area |
| --- | --- |
| 50 cm/s | 20% |
| 70 cm/s | 15% |
| 85 cm/s | 8% |

It is preferable that the amounts of application of the Flow-void pulses 1504, 1505, and 1506 be different amounts in the respective axes of Gr, Gp, and Gs. As the amount of application of the Flow-void pulse 1505 in the Gp direction, for example, 20% of the area of the half of the readout gradient magnetic field pulse 1501 is applied. As the amount of application of the Flow-void pulse 1506 in the GS direction, it is preferable to set the minimum amount of slice crusher application, which does not cause artifacts by Stimulated Echo, by adjusting the amount of slice crusher application.

In addition, as shown in FIG. 16(b), the amount of application of the Flow-comp pulses 1502 and 1503 in the Gr direction is reduced by the amount of application, which is equal to the amount of application of the Flow-void pulse 1504, according to the application of the Flow-void pulse 1504 in the Gr direction. Similarly, the amount of application of gradient magnetic field pulses 1601 and 1602 in the Gp direction is reduced by the amount of application of the Flow-void pulse 1505 in the Gp direction. The amount of application of gradient magnetic field pulses 1604 and 1605 in the Gs direction is increased by the amount of application of the Flow-void pulse 1506 in the Gs direction.

In step 1105, the imaging control section 404 passes to the sequencer 4 the imaging conditions set and input by the operator in step 1101 and TD1b calculated in step 1404, so that the sequencer 4 executes the FSE method sequence 201 with the added Flow-comp pulses 1502 and 1503 as shown in FIGS. 15 and 16(a). On the basis of the parameters passed, the sequencer 4 detects an electrocardiographic waveform from an object and repeats the imaging sequence at the diastolic timing of TD1b from an R wave, thereby measuring an echo signal based on the FSE method sequence. Then, the imaging control section 404 passes to the sequencer 4 the Flow-void pulses 1504, 1505, and 1506 and TD1a calculated in step 1404, so that the sequencer 4 executes the FSE method sequence 201 with the added Flow-comp pulses 1502 and 1503 and Flow-void pulses 1504, 1505, and 1506 as shown in FIGS. 15 and 16(a). On the basis of the parameters passed, the sequencer 4 detects an electrocardiographic waveform from an object and repeats the imaging sequence at the systole timing of TD1a from an R wave, thereby measuring an echo signal based on the FSE method sequence.

In step 1106, the image reconstruction section 405 reconstructs an image using the diastolic echo signal measured in step 1105. As a result, an image (arteriovenous image) in which an artery and a vein are included is acquired. In addition, the image reconstruction section 405 reconstructs an image using the systolic echo signal measured in step 1105. In the systolic echo signal, a signal from the artery is suppressed by the Flow-void pulses 1504, 1505, and 1506. Accordingly, an image in which only the vein is included is acquired.

In step 1107, an artery image is acquired by removing a vein image by performing differential processing on a diastolic arteriovenous image and a systolic vein image. In this case, since the weighting coefficient is experientially set in the related art, it is not possible to remove a vein image depending on the state of the object.

In the fourth embodiment, the weighting coefficient is calculated on the basis of the blood flow speed of the vein and the amount of application of the Flow-void pulse 1504 determined in step 1404. Accordingly, since a vein image can be removed with high accuracy by differential processing, an artery image can be acquired. That is, although the Flow-void pulse 1504 applied in systole disperses the phase of the spin of the blood flow of the artery with high blood flow speed more largely, Flow-void pulse 1504 applied in systole also disperses the phase of the spin of the blood flow of the vein with low blood flow speed according to the blood flow speed. For this reason, even though the blood flow speed of the systolic vein and the diastolic vein is almost constant, the signal strength of the systolic vein image is suppressed more than that of a diastolic image according to the amount of application of the Flow-void pulse 1504 and the blood flow speed. The degree by which the Flow-void pulse 1504 suppresses the signal amount of a vein depends on the size of the Flow-void pulse 1504 and the blood flow speed of the vein. In the fourth embodiment, therefore, a function F having the size of the Flow-void pulse 1504 and the blood flow speed Vb of a vein calculated in step 1402 as input values and the weighting coefficient W as an output value is created by calculation or the like in advance, and the weighting coefficient W is calculated by operation. Alternatively, it is also possible to create the following conversion table, which matches the blood flow speed of a vein to the weighting coefficient, by calculation or the like in advance for each size of the Flow-void pulse 1504 and to apply the result to differential processing.

TABLE 2

| Blood flow speed | Weighting coefficient |
| --- | --- |
| 20 to 25 cm/s | 0.7 |
| 15 to 20 cm/s | 0.8 |
| 8 to 15 cm/s | 0.9 |
| 8 cm/s or less | 1.0 |

In both methods, an artery image can be separated with high accuracy by multiplying an arteriovenous image acquired from the diastolic echo signal by the weighting coefficient and taking a difference from the systolic vein image.

In the fourth embodiment, by executing the FSE method sequence in TD1a and TD1b acquired from the PC method image, a systolic FSE image and a diastolic FSE image can be acquired with high accuracy without troubling the operator. In addition, since the systolic blood flow speed can be acquired from the PC method image, the Flow-void pulse 1504 can be applied with the appropriate amount of application. Accordingly, an artery image can be suppressed from the systolic FSE image.

In addition, since a weighting coefficient can be calculated from the Flow-void pulse 1504, weighting can be made according to the systolic vein image suppressed by the Flow-void pulse 1504. Therefore, by taking a difference between the diastolic image and the systolic image using this weighting coefficient, a vein image can be separated with high accuracy and an artery image can be acquired accordingly.

In addition, when detecting systole and diastole in step 1403, it is also possible to examine the blood flow speed and the cardiac time phase in detail in order to do that with higher accuracy. For example, maximum and minimum values, their absolute values, and cardiac time phases when the maximum and minimum values are obtained are derived from the graph in FIG. 13(b). The larger extreme value is selected by comparing the absolute values of the maximum and minimum values. The larger extreme value is set as the systolic blood flow speed, and the cardiac time phase when the blood flow speed is obtained is set as the interval TD1a from an R wave in systolic imaging. Then, the diastolic blood flow speed is calculated. For example, in maximum or minimum values excluding the extreme values determined to be systole, an extreme value which has the opposite polarity to the extreme values determined to be systole and whose absolute value is minimum is set as the diastolic blood flow speed, and the cardiac time phase when the blood flow speed is obtained is set as the interval TD1b from an R wave in diastole. In addition, the method of determining diastole is not limited to the method of noting the maximum and minimum values described above. For example, it is also possible to check the range of elapsed time from an R wave whose blood flow speed is equal to or less than ±5 cm/s, which is sufficiently low, and set the elapsed time in the middle of its range as the interval TD1b. Thus, by determining the imaging conditions using the graph shown in FIG. 13(b), the image quality can be stabilized even if there is an individual difference and a difference between parts. The above is an example of examining the blood flow speed in detail.

In addition, it is also possible to use a method of examining the cardiac time phase in detail. For example, a threshold value is set for the cardiac cycle. That is, for the systolic cardiac time phase and the diastolic cardiac time phase derived by the procedure already described, whether the difference between the cardiac time phases is between 1/3 to 2/3 of the cardiac cycle is set as a threshold value. When the cardiac time phases deviate from this range, the cardiac time phases are not used as systole and diastole.

Alternatively, it is also possible to determine automatically the region of interest 1301 for creating the graph shown in FIG. 13(b). As a typical method, determination of the blood flow speed and the diastole and systole already described is performed beforehand, and a region satisfying the conditions set in advance is determined to be a region equivalent to the artery. That is, a three-dimensional array having a coordinate value (X, Y) of a PC image and a cardiac time phase as dimensions is created. Elements of the three-dimensional array are the value of a pixel in each coordinate value of the PC image, that is, blood flow speed. Focusing on the value of this blood flow speed, most simply, maximum and minimum values of the pixel values and cardiac time phases when the maximum and minimum values are obtained are derived. Then, a pixel whose difference between the maximum value and the minimum value is greater than a predetermined threshold value is determined to be a pixel equivalent to the artery. Then, for pixels extracted as an artery in the determination, when the extracted pixels are adjacent to each other, it is determined that the extracted pixels are pixels in the same artery. Accordingly, this region is regarded as a region including a plurality of pixels, and the region is extended. This extended region is set as the above-described region of interest 1301 designated by the operator, and then the same processing is applied. When a plurality of extended regions are present, a region where a difference between the systolic blood flow speed and the diastolic blood flow speed is largest is regarded as the region of interest 1301 designated by the operator.

In addition, since the blood flow speed changes greatly with the age of an object or the presence or absence of disease, the characteristic amounts when performing the automatic determination are not limited to the above-described maximum and minimum values, local maximum and minimum values, and their absolute values. In addition, in the present invention, a graph of speed and time may be displayed or may not be displayed, and a region of interest using a PC method image may be displayed or may not be displayed. That is, operator's input and operator's checking of the position of an artery and the cardiac time phases of diastole and systole may be performed or may not be performed. Preferably, display or non-display can be changed by determination of the operator. Alternatively, Only when the diastolic blood flow speed, the systolic blood flow speed, and the cardiac time phase that realizes the blood flow speed do not satisfy the conditions set in advance or when it is determined that the reliability is low, it is preferable to display a PC image or the graph of speed and time so that the operator checks it. Alternatively, it is possible to use the above-described method in which the operator inputs the region of interest 1301 using a displayed PC method image, or the operator may input the delay time TD1a and TD1b from electrocardiographic R waves equivalent to diastole and systole and the blood flow speed in the same cardiac time phase using the displayed graph of blood flow speed and time.

Fifth Embodiment

Figure 17:
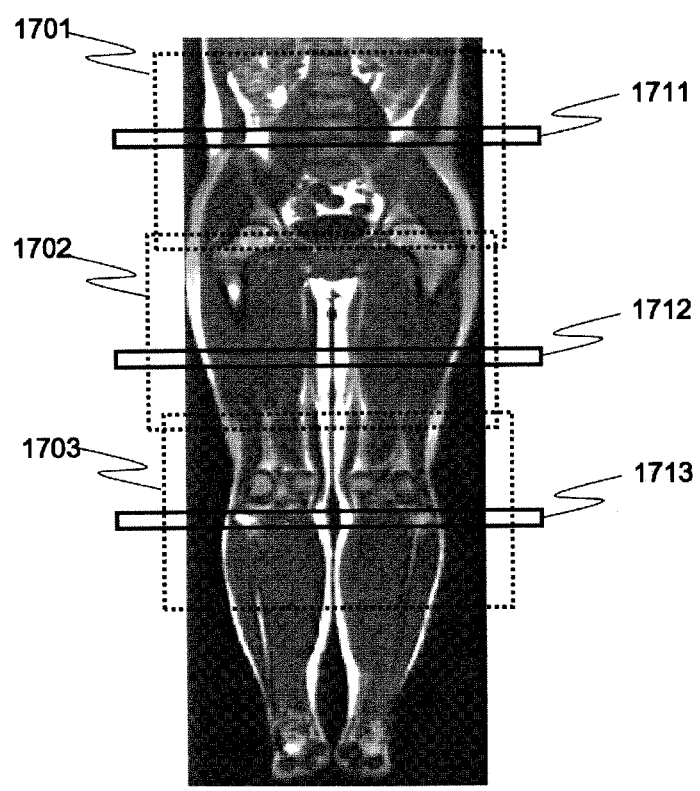
FIG. 17 is an explanatory view showing stations 1701 to 1703, which are imaged by the FSE method sequence of the imaging sequences related to a fifth embodiment, and an imaging region of the PC method sequence.
Figure 18:
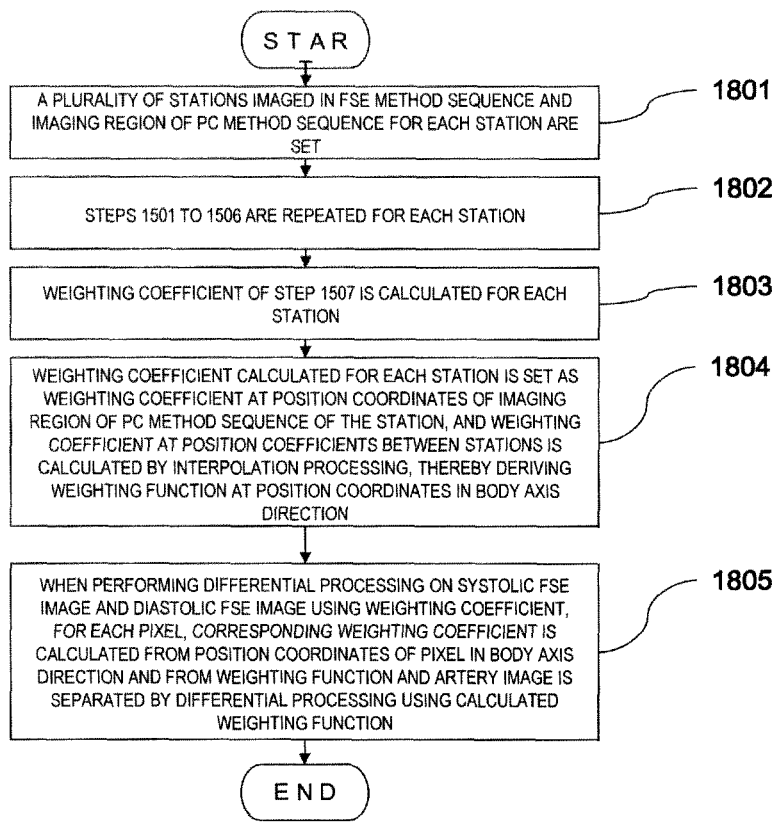
FIG. 18 is a flow chart showing the entire process flow of the imaging method in the fifth embodiment.

An MRI apparatus and a blood vessel image capturing method of a fifth embodiment of the present invention will be described using FIGS. 17 and 18.

In the fourth embodiment, one weighting coefficient is determined for the FSE method image. When a leg or the like is set as an object to be imaged, it is not possible to cover the target region with the normal field of view. For this reason, movement of the bed on which an object is placed and imagine of a target part are repeated. Such imaging is generally called multi-station imaging. For example, as shown in FIG. 17, a target part is set like pelvis in a first station 1701, thighs in a second station 1702, knees in a third station 1703, and ankles in a fourth station (step 1801). Although there is one imaging region 212 of the PC method per one station in the fourth embodiment, imaging regions 1711 to 1713 are set for each station which images a target part in the fifth embodiment. In this manner, it is possible to calculate one weighting coefficient for each station.

Then, in steps 1802 and 1803, steps 1101 to 1106 of the fourth embodiment are performed for each station, thereby calculating the weighting coefficients at the position coordinates of the imaging regions 1711 to 1713 by the PC method.

In addition, the blood flow speed becomes slow gradually towards the periphery. In step 1804, therefore, a weighting function having the position coordinates as a variable is calculated in the body axis direction by applying interpolation processing to the weighting coefficient at each position coordinates calculated in step 1803. Then, in step 1805, weighted differential processing on the systolic FSE image and the diastolic FSE image is executed using the weighting coefficient at each position coordinates acquired in step 1804. For example, the correspondence of an imaging part (station) and the position coordinates in the body axis direction, blood flow speed, and a weighting coefficient is shown in the following Table 3.

TABLE 3

|  | Position coordinates in body axis direction | Blood flow speed of vein | Weighting coefficient |
| --- | --- | --- | --- |
| Pelvis (first station) | 0 cm (reference) | 25 cm/s | 0.7 |
| Thighs (second station) | 30 cm | 20 cm/s | 0.8 |
| Knees (third station) | 55 cm | 12 cm/s | 0.9 |
| Ankles (fourth station) | 80 cm | 8 cm/s | 1.0 |

In addition, a result when the blood flow speed at the same position as the position coordinates in the body axis direction is derived by interpolation processing and the weighting coefficient are calculated with reference to the measurement data is shown in the following Table 4, for example.

TABLE 4

| Coordinates | Blood flow speed | Weighting coefficient |
| --- | --- | --- |
| 0 cm | 25 cm/s (measured) | 0.7 |
| 15 cm | 22.5 cm/s (estimated) | 0.73 |
| 30 cm | 20 cm/s (measured) | 0.8 |
| 40 cm | 17 cm/s (estimated) | 0.8 |
| 50 cm | 14 cm/s (estimated) | 0.85 |
| 55 cm | 12 cm/s (measured) | 0.9 |
| 65 cm | 9 cm/s (estimated) | 1.0 |
| 80 cm | 8 cm/s (measured) | 1.0 |

Thus, in the fifth embodiment, the weighting coefficient can be set for each position coordinates. Accordingly, an artery image of an object part in a wide range in which the blood flow speed becomes slow gradually towards the periphery can be separated with high accuracy.

In addition, it is also possible to create a weighting function by fitting using, for example, a linear approximation straight line as sampling points of the weighting coefficient and to apply the weighting function at the time of differential processing.

As described above, in the MRI apparatus and the blood vessel image capturing method of the present embodiment, a plurality of images (an FSE image and a PC image) with different characteristics are captured using different imaging methods a PC method and an FSE method), and an artery and a vein are separated from each other on the image (FSE image) acquired by the other imaging method (FSE method) using the blood flow information extracted by the one imaging method (PC method). As a result, it is possible to improve the separability of an artery and a vein.

In addition, since a user does not need to select a diastolic image and a systolic image, it is possible to reduce the burden on the user and to separate an artery from a vein stably.

REFERENCE SIGNS LIST

1: object
2: static magnetic field generation system
3: gradient magnetic field generation system
4: sequencer
5: signal transmission system
6: signal receiving system
7: signal processing system
8: central processing unit (CPU)
9: gradient magnetic field coil
10: gradient magnetic field power supply
11: high-frequency oscillator
12: modulator
13: high-frequency amplifier
14a: high-frequency coil (transmission coil)
14b: high-frequency coil (receiving coil)
15: signal amplifier
16: quadrature phase detector
17: A/D converter
18: magnetic disk
19: optical disc
20: display
23: track ball or mouse
24: keyboard
27: electrocardiogram and pulse wave monitor

The invention claimed is:

1. A magnetic resonance imaging apparatus comprising:
a measurement control section which controls measurement of an echo signal from a desired region of an object using a predetermined imaging sequence;
a body motion information detection section which detects an electrocardiogram of the object; and
an image reconstruction section which reconstructs an image using the echo signal,
wherein the imaging sequence is obtained by combining a first sequence portion for measuring a first echo signal used for acquisition of the image with a second sequence portion for measuring a second echo signal used for acquisition of blood flow information of the object,
the measurement control section executes the first sequence portion in diastole and the second sequence portion in systole within a cardiac cycle of the object, and
a blood flow information acquisition section which acquires the blood flow information using the second echo signal and an artery and vein separation section which extracts at least one of an artery and a vein in the image, which is reconstructed using the first echo signal, using the blood flow information are provided.

2. The magnetic resonance imaging apparatus according to claim 1,
wherein the measurement control section sets a plurality of cycle periods of periodic body motion of the object as a repetition period of at least a part of the imaging sequence.

3. The magnetic resonance imaging apparatus according to claim 1,
wherein the measurement control section executes the first sequence portion in only diastole and the second sequence portion in only systole within a cardiac cycle of the object.

4. The magnetic resonance imaging apparatus according to claim 1,
wherein the measurement control section performs the first and second sequence portions in different cardiac beat periods.

5. The magnetic resonance imaging apparatus according to claim 1,
wherein the second sequence portion includes a PC method sequence or a TOF method sequence.

6. The magnetic resonance imaging apparatus according to claim 1,
wherein the image reconstruction section reconstructs a blood flow information image including the blood flow information using the second echo signal, and
a pixel extraction section which extracts a pixel of the artery or the vein on the blood flow information image, a same position pixel extraction section which extracts a pixel at the same position as a pixel position of the extracted pixel of the artery or the vein on an image reconstructed using the first echo signal, and a blood vessel region extraction section which extracts as the artery or the vein a region including a pixel at the same position extracted on the image reconstructed using the first echo signal are provided.

7. A blood vessel image capturing method of acquiring a blood vessel image of an object, said method comprising:
a measurement control step of controlling measurement of echo signals using a predetermined imaging sequence obtained by combining a first sequence portion for measuring a first echo signal used for acquisition of an image of the object with a second sequence portion for measuring a second echo signal used for acquisition of blood flow information of the object;
a body motion information detection step of detecting an electrocardiogram of the object;
a measurement step of measuring the first and second echo signals by repeating the imaging sequence in synchronization with cardiac cycles of the object, wherein
the measurement control step executes the first sequence portion in diastole and the second sequence portion in systole, within a cardiac cycle of the object;
a blood flow information acquisition step of acquiring the blood flow information using the second echo signal; and
a blood vessel image acquisition step of extracting at least one of an artery and a vein in an image, which is reconstructed using the first echo signal, using the blood flow information.

8. The magnetic resonance imaging apparatus according to claim 1,
wherein the artery and vein separation section extracts a pixel position on an image reconstructed from the first echo signal corresponding to a positional information of a pixel extracted on an image reconstructed from the second echo signal, and extracts at least one of an artery and a vein by region growing method starting from the extracted pixel position in the image reconstructed from the first echo signal.

\* \* \* \* \*